(12) United States Patent
Genova et al.

(10) Patent No.: US 7,913,365 B2
(45) Date of Patent: Mar. 29, 2011

(54) METHOD OF FORMING BARBS ON A SUTURE AND APPARATUS FOR PERFORMING SAME

(75) Inventors: Perry A. Genova, Chapel Hill, NC (US); Robert C. Williams, III, Raleigh, NC (US); Warren Jewett, Cary, NC (US); Matthew A. Megaro, Chapel Hill, NC (US)

(73) Assignee: Quill Medical, Inc.

( * ) Notice: Subject to any disclaimer, the term of this patent is extended or adjusted under 35 U.S.C. 154(b) by 855 days.

(21) Appl. No.: 11/691,845

(22) Filed: Mar. 27, 2007

(65) Prior Publication Data

US 2007/0187861 A1 Aug. 16, 2007

Related U.S. Application Data

(63) Continuation of application No. 10/486,123, filed as application No. PCT/US02/27525 on Aug. 29, 2002, now Pat. No. 7,225,512, which is a continuation-in-part of application No. 09/943,733, filed on Aug. 31, 2001, now Pat. No. 6,848,152.

(51) Int. Cl.
*B21F 25/00* (2006.01)
*B29C 41/24* (2006.01)
*A61B 17/04* (2006.01)

(52) U.S. Cl. ............... 29/7.1; 164/165; 606/228

(58) Field of Classification Search ............ 29/7.1, 29/7.2; 264/165; 83/651; 606/228, 215, 606/224, 216

See application file for complete search history.

(56) References Cited

U.S. PATENT DOCUMENTS

| | | | |
|---|---|---|---|
| 709,392 | A | 9/1902 | Brown |
| 733,723 | A | 7/1903 | Lukens |
| 789,401 | A | 5/1905 | Acheson |
| 816,026 | A | 3/1906 | Meier |
| 879,758 | A | 2/1908 | Foster |
| 1,142,510 | A | 6/1915 | Engle |
| 1,248,825 | A | 12/1917 | Dederer |
| 1,321,011 | A | 11/1919 | Cottes |
| 1,728,316 | A | 9/1929 | von Wachenfeldt |
| 1,886,721 | A | 11/1932 | O'Brien |
| 2,094,578 | A | 10/1937 | Blumenthal et al. |
| 2,201,610 | A | 5/1940 | Dawson, Jr. |
| 2,232,142 | A | 2/1941 | Schumann |
| 2,254,620 | A | 9/1941 | Miller |
| 2,355,907 | A | 8/1944 | Cox |

(Continued)

FOREIGN PATENT DOCUMENTS

CN 2640420 9/2004

(Continued)

OTHER PUBLICATIONS

A. R. McKenzie, "An experimental multiple barbed suture for the long flexor tendons of the palm and fingers", The Journal of Bone and Joint Surgery, Aug. 1967, pp. 440-447, vol. 49B, No. 3.

(Continued)

*Primary Examiner* — John C Hong
(74) *Attorney, Agent, or Firm* — Angiotech

(57) ABSTRACT

A method of making a barbed suture by varying the blade geometry and/or the movement of the blade when cutting a suture is disclosed. The method can also be accomplished with a cutting device to create a plurality of barbs on the exterior of surgical suture. The barbs produced using the method with the cutting device can be the same or random configurations.

52 Claims, 23 Drawing Sheets

U.S. PATENT DOCUMENTS

| | | |
|---|---|---|
| 2,421,193 A | 5/1947 | Gardner |
| 2,472,009 A | 5/1949 | Gardner |
| 2,572,936 A | 10/1951 | Kulp et al. |
| 2,684,070 A | 7/1954 | Kelsey |
| 2,779,083 A | 1/1957 | Eaton |
| 2,814,296 A | 11/1957 | Everett |
| 2,817,339 A | 12/1957 | Sullivan |
| 2,866,256 A | 12/1958 | Matlin |
| 2,910,067 A | 10/1959 | White |
| 2,988,028 A | 6/1961 | Alcamo |
| 3,003,155 A | 10/1961 | Mielzynski et al. |
| 3,068,869 A | 12/1962 | Shelden et al. |
| 3,068,870 A | 12/1962 | Levin |
| 3,123,077 A | 3/1964 | Alcamo |
| 3,166,072 A | 1/1965 | Sullivan, Jr. |
| 3,187,752 A | 6/1965 | Glick |
| 3,209,754 A | 10/1965 | Brown |
| 3,214,810 A | 11/1965 | Mathison |
| 3,221,746 A | 12/1965 | Noble |
| 3,234,636 A | 2/1966 | Brown |
| 3,273,562 A | 9/1966 | Brown |
| 3,352,191 A | 11/1967 | Crawford |
| 3,378,010 A | 4/1968 | Codling et al. |
| 3,385,299 A | 5/1968 | Le Roy |
| 3,494,006 A | 2/1970 | Brumlik |
| 3,525,340 A | 8/1970 | Gilbert |
| 3,527,223 A | 9/1970 | Shein |
| 3,586,002 A | 6/1971 | Wood |
| 3,608,095 A | 9/1971 | Barry |
| 3,608,539 A | 9/1971 | Miller |
| 3,646,615 A | 3/1972 | Ness |
| 3,683,926 A | 8/1972 | Suzuki |
| 3,700,433 A | 10/1972 | Duhl |
| 3,716,058 A | 2/1973 | Tanner, Jr. |
| 3,720,055 A | 3/1973 | de Mestral et al. |
| 3,825,010 A | 7/1974 | McDonald |
| 3,833,972 A | 9/1974 | Brumlik |
| 3,845,641 A | 11/1974 | Waller |
| 3,847,156 A | 11/1974 | Trumble |
| 3,918,455 A | 11/1975 | Coplan |
| 3,981,051 A | 9/1976 | Brumlik |
| 3,981,307 A | 9/1976 | Borysko |
| 4,006,747 A | 2/1977 | Kronenthal et al. |
| 4,043,344 A | 8/1977 | Landi et al. |
| 4,069,825 A | 1/1978 | Akiyama |
| 4,073,298 A | 2/1978 | Le Roy |
| 4,198,734 A | 4/1980 | Brumlik |
| 4,259,959 A | 4/1981 | Walker |
| 4,300,424 A | 11/1981 | Flinn et al. |
| 4,311,002 A | 1/1982 | Hoffmann et al. |
| 4,316,469 A | 2/1982 | Kapitanov |
| 4,317,451 A | 3/1982 | Cerwin et al. |
| 4,428,376 A | 1/1984 | Mericle |
| 4,430,998 A | 2/1984 | Harvey et al. |
| 4,434,796 A | 3/1984 | Karapetian et al. |
| 4,454,875 A | 6/1984 | Pratt et al. |
| 4,467,805 A | 8/1984 | Fukuda |
| 4,492,075 A | 1/1985 | Faure |
| 4,493,323 A | 1/1985 | Albright et al. |
| 4,505,274 A | 3/1985 | Speelman |
| 4,510,934 A | 4/1985 | Batra |
| 4,531,522 A | 7/1985 | Bedi et al. |
| 4,548,202 A | 10/1985 | Duncan |
| 4,610,251 A | 9/1986 | Kumar |
| 4,635,637 A | 1/1987 | Schreiber |
| 4,637,380 A | 1/1987 | Orejola |
| 4,653,486 A | 3/1987 | Coker |
| 4,669,473 A | 6/1987 | Richards et al. |
| 4,676,245 A | 6/1987 | Fukuda |
| 4,719,917 A | 1/1988 | Barrows et al. |
| 4,776,337 A | 10/1988 | Palmaz |
| 4,832,025 A | 5/1989 | Coates |
| 4,841,960 A | 6/1989 | Garner |
| 4,873,976 A | 10/1989 | Schreiber |
| 4,887,601 A | 12/1989 | Richards |
| 4,895,148 A | 1/1990 | Bays et al. |
| 4,900,605 A | 2/1990 | Thorgersen et al. |
| 4,905,367 A | 3/1990 | Pinchuk et al. |
| 4,930,945 A | 6/1990 | Arai et al. |
| 4,948,444 A | 8/1990 | Schutz et al. |
| 4,950,285 A | 8/1990 | Wilk |
| 4,976,715 A | 12/1990 | Bays et al. |
| 4,981,149 A | 1/1991 | Yoon et al. |
| 4,994,073 A | 2/1991 | Green |
| 4,997,439 A | 3/1991 | Chen |
| 5,002,562 A | 3/1991 | Oberlander |
| 5,007,921 A | 4/1991 | Brown |
| 5,007,922 A | 4/1991 | Chen et al. |
| 5,026,390 A | 6/1991 | Brown |
| 5,047,047 A | 9/1991 | Yoon |
| 5,053,047 A | 10/1991 | Yoon |
| 5,084,063 A | 1/1992 | Korthoff |
| 5,102,418 A | 4/1992 | Granger et al. |
| 5,102,421 A | 4/1992 | Anspach, Jr. |
| 5,103,073 A | 4/1992 | Danilov et al. |
| 5,112,344 A | 5/1992 | Petros |
| 5,123,911 A | 6/1992 | Granger et al. |
| 5,123,913 A | 6/1992 | Wilk et al. |
| 5,123,919 A | 6/1992 | Sauter et al. |
| 5,127,413 A | 7/1992 | Ebert |
| 5,133,738 A | 7/1992 | Korthoff et al. |
| 5,141,520 A | 8/1992 | Goble et al. |
| 5,156,788 A | 10/1992 | Chesterfield et al. |
| 5,192,302 A | 3/1993 | Kensey et al. |
| 5,207,694 A | 5/1993 | Broome |
| 5,217,494 A | 6/1993 | Coggins et al. |
| 5,222,976 A | 6/1993 | Yoon |
| 5,224,946 A | 7/1993 | Hayhurst et al. |
| 5,246,441 A | 9/1993 | Ross et al. |
| 5,258,013 A | 11/1993 | Granger et al. |
| 5,269,783 A | 12/1993 | Sander |
| 5,292,326 A | 3/1994 | Green et al. |
| 5,320,629 A | 6/1994 | Noda et al. |
| 5,330,503 A | 7/1994 | Yoon |
| 5,341,922 A | 8/1994 | Cerwin et al. |
| 5,342,376 A | 8/1994 | Ruff |
| 5,352,515 A | 10/1994 | Jarrett et al. |
| 5,372,146 A | 12/1994 | Branch |
| 5,374,268 A | 12/1994 | Sander |
| 5,374,278 A | 12/1994 | Chesterfield et al. |
| 5,395,126 A | 3/1995 | Tresslar |
| 5,411,523 A | 5/1995 | Goble |
| 5,414,988 A | 5/1995 | DiPalma et al. |
| 5,425,746 A | 6/1995 | Proto et al. |
| 5,425,747 A | 6/1995 | Brotz |
| 5,450,860 A | 9/1995 | O'Connor |
| 5,500,000 A | 3/1996 | Feagin et al. |
| 5,500,991 A | 3/1996 | Demarest et al. |
| 5,520,691 A | 5/1996 | Branch |
| 5,533,982 A | 7/1996 | Rizk et al. |
| 5,536,582 A | 7/1996 | Prasad et al. |
| 5,546,957 A | 8/1996 | Heske |
| 5,584,859 A | 12/1996 | Brotz |
| 5,601,557 A | 2/1997 | Hayhurst |
| 5,683,417 A | 11/1997 | Cooper |
| 5,697,976 A | 12/1997 | Chesterfield et al. |
| 5,702,462 A | 12/1997 | Oberlander |
| 5,716,376 A | 2/1998 | Roby et al. |
| 5,722,991 A | 3/1998 | Colligan |
| 5,887,594 A | 3/1999 | LoCicero, III |
| 5,897,572 A | 4/1999 | Schulsinger et al. |
| 5,931,855 A | 8/1999 | Buncke |
| 5,964,783 A | 10/1999 | Grafton et al. |
| 5,972,024 A | 10/1999 | Northrup, III et al. |
| 5,984,933 A | 11/1999 | Yoon |
| 6,012,216 A | 1/2000 | Esteves et al. |
| 6,027,523 A | 2/2000 | Schmieding |
| 6,056,778 A | 5/2000 | Grafton et al. |
| 6,083,244 A | 7/2000 | Lubbers et al. |
| 6,102,947 A | 8/2000 | Gordon |
| 6,163,948 A | 12/2000 | Esteves et al. |
| 6,241,747 B1 | 6/2001 | Ruff |
| 6,251,143 B1 | 6/2001 | Schwartz et al. |
| 6,270,517 B1 | 8/2001 | Brotz |
| 6,443,962 B1 | 9/2002 | Gaber |
| 6,478,809 B1 | 11/2002 | Brotz |
| RE37,963 E | 1/2003 | Thal |

| | | |
|---|---|---|
| 6,599,310 B2 | 7/2003 | Leung et al. |
| 6,645,226 B1 | 11/2003 | Jacobs et al. |
| 6,773,450 B2 | 8/2004 | Leung et al. |
| 6,848,152 B2 | 2/2005 | Genova et al. |
| 6,905,484 B2 | 6/2005 | Buckman et al. |
| 7,056,331 B2 | 6/2006 | Kaplan et al. |
| 7,226,468 B2 | 6/2007 | Ruff |
| 2003/0149447 A1 | 8/2003 | Morency et al. |
| 2004/0060409 A1 | 4/2004 | Leung et al. |
| 2004/0060410 A1 | 4/2004 | Leung et al. |
| 2004/0088003 A1 | 5/2004 | Leung et al. |
| 2004/0106949 A1 | 6/2004 | Cohn et al. |
| 2004/0138683 A1 | 7/2004 | Shelton et al. |
| 2004/0193191 A1 | 9/2004 | Starksen et al. |
| 2005/0203576 A1 | 9/2005 | Sulamanidze et al. |
| 2006/0079935 A1 | 4/2006 | Kolster |
| 2006/0135994 A1 | 6/2006 | Ruff et al. |
| 2006/0135995 A1 | 6/2006 | Ruff et al. |
| 2007/0005109 A1 | 1/2007 | Popadiuk et al. |
| 2007/0005110 A1 | 1/2007 | Collier et al. |
| 2007/0038249 A1 | 2/2007 | Kolster |
| 2007/0208355 A1 | 9/2007 | Ruff |
| 2007/0224237 A1 | 9/2007 | Hwang et al. |

FOREIGN PATENT DOCUMENTS

| | | |
|---|---|---|
| DE | 1810800 | 6/1970 |
| DE | 4302895 | 8/1994 |
| DE | 19618891 | 4/1997 |
| DE | 19833703 | 2/2000 |
| EP | 0428253 | 5/1991 |
| EP | 0576337 | 12/1993 |
| EP | 0612504 | 11/1997 |
| EP | 0826337 | 3/1998 |
| EP | 0839499 | 5/1998 |
| EP | 0913123 | 5/1999 |
| EP | 1075843 | 2/2001 |
| FR | 2619129 | 2/1989 |
| FR | 9208059 | 12/1993 |
| FR | 2693108 | 1/1994 |
| GB | 1091282 | 11/1967 |
| GB | 1428560 | 3/1976 |
| GB | 1506362 | 4/1978 |
| JP | 54116419 | 9/1979 |
| JP | 01113091 | 5/1989 |
| JP | 10085225 | 4/1998 |
| JP | 11332828 | 12/1999 |
| NZ | 501224 | 3/2002 |
| NZ | 531262 | 6/2002 |
| RU | 2139690 | 10/1999 |
| SU | 1745214 | 7/1992 |
| SU | 1752358 | 8/1992 |
| WO | 96/06565 | 3/1996 |
| WO | 98/52473 | 11/1998 |
| WO | 99/21488 | 5/1999 |
| WO | 00/51658 | 9/2000 |
| WO | 03/001979 | 1/2003 |
| WO | 03/017850 | 3/2003 |
| WO | 03/045255 | 6/2003 |
| WO | 03/103733 | 12/2003 |
| WO | 2004/014236 | 2/2004 |
| WO | 2004/030520 | 4/2004 |
| WO | 2004/030704 | 4/2004 |
| WO | 2004/030705 | 4/2004 |
| WO | 2006/061868 | 6/2006 |
| WO | 2007/133103 | 11/2007 |

OTHER PUBLICATIONS

B. G. Sulzle, Inc., "Drilled end surgical needles", Syracuse, New York.

M. A. Sulamanidze, T. G. Paikidze, & G. M. Sulamanidze, "Facial lifting with 'Aptos' threads", http://www.fonendo.com, Jul. 18, 2001, pp. 1-4.

Philip P. Dattilo Jr., Martin W. King, Nancy L. Cassill, & Jeffrey C. Leung, "Medical textiles: application of an absorbable barbed bi-directional surgical suture", Journal of Textile and Apparel, Technology and Management, Spring 2002, vol. 2, Issue 2.

CCPR Centro De Cirurgia Plastica E Reabilitacao, "Up Lifting (Aptos Threads)", http://www.ccpr.com.br/upl-l.htm, Aug. 19, 2002, pp. 1-2.

Hougtao Han, Lee E. Weiss, & Michael L. Reed, "Mating and piercing micromechanical structures for surface bonding applications", Micro Electric Mechanical Systems (MEMS-91), Jan. 31-Feb. 2, 1991, Nara, Japan, CH2597-9/91, pp. 253-258.

H. J. Buncke Jr. & W. P. Schulz, "The suture repair of one-millimeter vessels", Micro-vascular Surgery, Report of First Conference, Oct. 6-7, 1966, pp. 24-35 (note p. 34).

M. A. Sulamanidze, P. F. Fournier, T. G. Paikidze, & G. M. Sulamanidze, "Removal of facial soft tissue ptosis with special threads", Dermatologic Surgery, May 2002, pp. 367-371, vol. 28.

Gregory L. Ruff, "Declaration of Dr. Gregory L. Ruff", Aug. 19, 2005.

M. A. Sulamanidze, M. A. Shiffman, T. G. Paikidze, G. M. Sulamanidze, & L. G. Gavashell, "Facial lifting with Aptos threads", International Journal of Cosmetic Surgery and Aesthetic Dermatology, 2001, pp. 1-8, No. 4.

G. M. Semenov, V. L. Petrishin, & M. V. Kovshova, "Surgical suture", 2001, Piter, Saint Petersburg, pp. 12-13 and 92-98.

U. W. Boenisch, K. J. Faber, M. Ciarelli, J. R. Steadman, & S. P. Arnoczky, "Pull-out strength and stiffness of meniscal repair using absorbable arrows or Ti-Cron vertical and horizontal loop sutures", American Journal of Sports Medicine, Sep.-Oct. 1999, pp. 626-631, vol. 27, Issue 5.

Philip P Dattilo Jr., Martin W. King, & Jeffrey C. Leung, "Tissue holding performance of knotless absorbable sutures", Society for Biomaterials 29th Annual Meeting Transactions, 2003, p. 101.

A. Schmid & F. Schmid, "The outspreading anchor cord. A material for arthroscopic suturing of a fresh anterior cruciate ligament rupture", Surgical Clinic of the University of Gottingen.

METHOD OF FORMING BARBS ON A SUTURE AND APPARATUS FOR PERFORMING SAME

RELATED APPLICATIONS

This application is a continuation application of U.S. patent application Ser. No. 10/486,123, filed Jul. 2, 2004, which claims priority benefits under 35 USC §371 to PCT/US02/27525 filed on Aug. 29, 2002, published on Mar. 6, 2003 under publication number WO 03/017850 A1 and claiming continuation-in-part priority benefits to U.S. patent application Ser. No. 09/943,733 filed Aug. 31, 2001, now U.S. Pat. No. 6,848,152, issued Feb. 1, 2005, the entire contents of all of which are incorporated herein by reference.

BACKGROUND

The invention relates to a method of barbing suture filament by varying the blade geometry and/or the movement of a blade when cutting a suture filament where the method can also be utilized to cut a plurality of axially spaced barbs on the exterior of sutures and an apparatus for performing this.

DESCRIPTION OF THE PRIOR ART

In the prior art, it is well known that surgical and traumatic wounds are typically closed with a filament introduced into the tissue by a needle attached to one end. Closure of the wound and holding tissues together supports healing and re-growth. What is typically used for this procedure is known as a suture.

A barbed suture is a one-way suture which allows passage of a needle-drawn suture in one direction through tissue, but not in the opposite direction. A barbed suture is generally an elongated body having a pointed leading end and a plurality of axially and circumferentially spaced barbs on the exterior surface of the elongated body.

In closing a wound with a barbed suture, the suture is passed through tissue at each of the opposed sides of a wound. Suture pairs are formed in which trailing ends of sutures are positioned generally in alignment at opposite sides of the wound. On insertion of each suture, the needle is pushed to extend out of the tissue at a point laterally remote from the wound, then the needle is pulled out to draw the suture to the desired position, and the suture is then severed from the needle. (Note that methods of using barbed sutures are disclosed in copending U.S. patent application Ser. No. 09/896,455, filed Jun. 29, 2001, entitled "Suture Method" and assigned to Quill Medical, Inc., the disclosure of which is incorporated herein by reference.) The advantage of using barbed sutures is that there is an ability to put tension in the tissue with the result of less slippage of the suture in the wound. The number of suture pairs is selected in accordance with the size of the wound and the strength required to hold the wound closed. Although tissue anchoring is easier done with a very pointed barb and a relatively skinny tip, better tissue holding results are obtained with a fuller tip barb.

In some circumstances of tissue repair, a random configuration of barbs on the exterior of the suture might be preferred. With as many barb angles as possible, superior wound holding would be achieved. However, in other circumstances where the wound or tissue repair needed is small, a small suture would be preferable. A small suture would require a reduced number of barbs on the exterior of the suture.

Various methods of cutting the barbs have been proposed (see e.g. U.S. Pat. No. 5,931,855). However, such methods have not been commercially exploited for reasons which are unclear.

It is seen from the foregoing that there is a need for a method of cutting barbs on the exterior of sutures with a minimum of difficulty and in a reliable and relatively economic fashion so as to allow for the wide spread commercialization of such sutures. Such a method should also be able to vary the size of the barbs, their location and depth to allow for variation thereof and virtuality of their application. The method should be able to cut a plurality of barbs with the positioning depending on the number of barbs needed. The need also exists for a device able to use the method described above which can provide a plurality of axially spaced barbs either in a random or similar configuration, with the configuration depending upon, among other things, the type of tissue being repaired.

SUMMARY OF THE INVENTION

It is therefore a principal object of the present invention to provide for a practical method of cutting barbs in a suture.

It is therefore a further object of the present invention to provide a method for cutting fuller tipped barbs of various sizes on the exterior of a suture.

It is therefore a still further object of the present invention to provide a method for cutting a plurality of axially spaced barbs on the exterior of a suture.

It is therefore a still further object of the present invention to provide a method for cutting a plurality of axially spaced barbs circumferentially about the exterior of a suture.

It is therefore a still further object of the present invention to provide a method for cutting a plurality of axially spaced barbs in similar or random configurations on the exterior of a suture.

It is therefore a yet further object of the invention to provide for an illustrative apparatus to perform this method.

To attain the objects described, there is provided a cutting method which produces suture barbs of varying sizes depending on the geometry of the blade being used and/or the movement of the blade when cutting into a suture. By altering the blade geometry and/or degree or trajectory of blade movement, the barbs can be made of varying sizes designed for various surgical applications. For example: for joining fat and relatively soft tissues, larger barbs are desired, whereas smaller barbs are more suited for collagen intensive tissues. Also, the use of a combination of large and small barbs on the same suture will ensure maximum anchoring properties wherein barb sizes are customized for each tissue layer.

The cutting method may be achieved with a cutting device disclosed herein. The device disclosed can produce six sets of barbs in staggered positions along the length of a suture, such that three sets of barbs are faced opposite to another three sets of barbs. Viewing the suture on a cross-sectional plane, the barb sets would be positioned either 120 or 180 degrees to each other, depending on the cutting method. Longitudinally, each barb cut would begin where the nearest one ends.

Compared with the method of cutting barbs in an untwisted state, using the twisted configuration can: simplify production equipment; produce a stronger suture; reduce production cycle time by at least a factor of three; and be easily scalable to smaller diameters and produce barbs in a spiral fashion rather than at 120 or 180 degrees.

By way of variations, slight modifications, and/or combinations of the methods of cutting with and without twisting the suture, barbs can be obtained with random configurations.

There are instances in tissue repair that the random configuration may be ideal to anchor tissues in as many barb angles as possible to provide superior wound holding properties. These and other objects and characteristics of the present invention will become apparent from the further disclosure to be made in the detailed description given below.

BRIEF DESCRIPTION OF THE DRAWINGS

Thus by the present invention its objects and advantages will be realized the description of which should be taken in conjunction with the drawings wherein.

DETAILED DESCRIPTION OF CERTAIN PREFERRED EMBODIMENTS

We refer now to the drawings in detail wherein like numerals refer to like elements throughout the several views.

The purpose of the present invention is to provide for an effective way of producing a barbed suture. In this regard, several different types of methods are disclosed which are directed to the cutting action of a blade on the suture to create the barbs. As will be described, the cutting action envisioned takes into account the movement of the blade and the blade geometry.

Essentially, the cutting of the suture with a blade takes into account three dimensions x-y-z of the suture 6. Each dimension is important and may be addressed by the cutting motion of the blade and/or the blade geometry. Depending on the blade geometry, the blade movement can have an effect in the other dimensions.

Figure 1A:
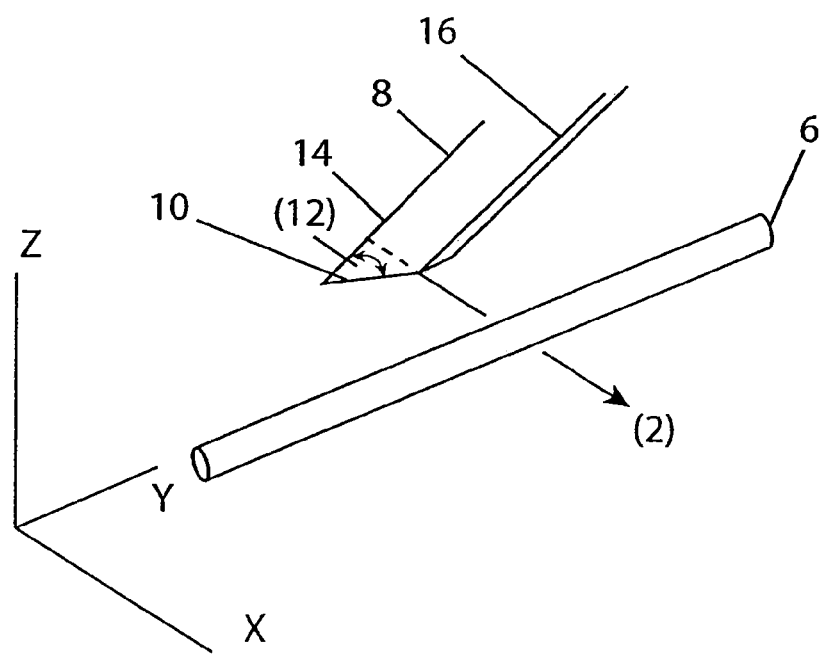
FIGS. 1A-F depict the cutting motion of a blade with one degree of freedom from movement and two degrees of freedom from blade geometry.

In this regard, FIG. 1A illustrates a consistent cutting motion of a blade 8 with one degree of freedom of movement and two degrees of freedom from blade geometry across a suture 6. One degree of freedom from movement is movement in one direction in a three-dimensional "x-y-z" layout. For FIG. 1A, direction (2) follows the lateral "x" axis in the cut of suture 6, with the movement of blade 8 in direction (2) before accomplishing a cut. An edge 10 of blade 8 has an angle, depicted as (12), in its blade geometry between the tips of sides 14, 16 of blade 8, as well as an angle (not shown) in its blade geometry between the top and bottom planes of blade 8. Such a geometry will cause an effect in the y and z dimensions (i.e. in the length and depth of the barb) just by the movement of blade 8 in the x direction.

Figure 1B:
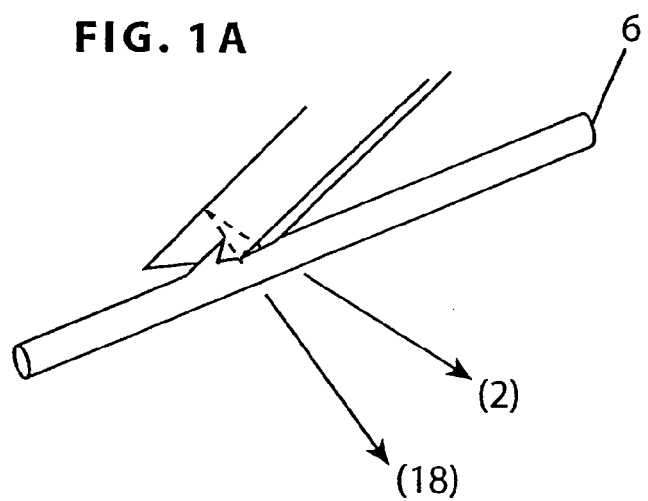
Figure 1C:
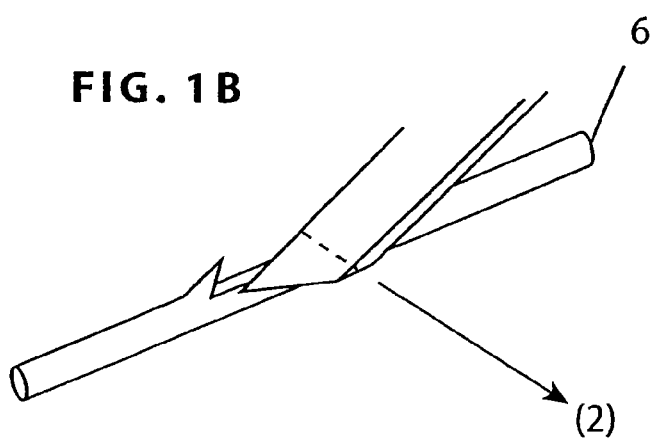

As shown in FIG. 1B, these angles allow a cut into suture 6 in the y and z directions during movement in direction (2). This cutting-into movement is depicted as resultant direction (18). FIG. 1C depicts the completed cut of suture 6 with a continued movement in direction (2) away from the suture 6.

Figure 1D:
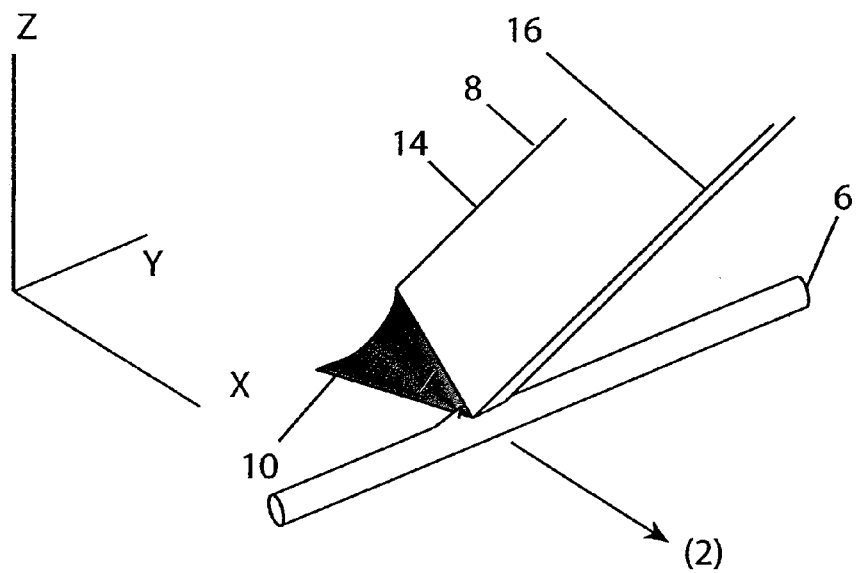

Similar to FIG. 1A, FIG. 1D illustrates a cutting motion of a blade 8 with one degree of freedom of movement and two degrees of freedom from blade geometry across a suture 6. In FIG. 1D, blade 8 is a hollow ground blade, in which edge 10 has an angle in its blade geometry between the tips of its sides 14, 16, as well as a concave or curved-in face in its blade geometry between the top and bottom planes of blade 8. Such a geometry will cause an effect in the y and z dimensions (i.e. in the length and depth of the barb) just by the movement of blade 8 in the x direction.

Figure 1E:
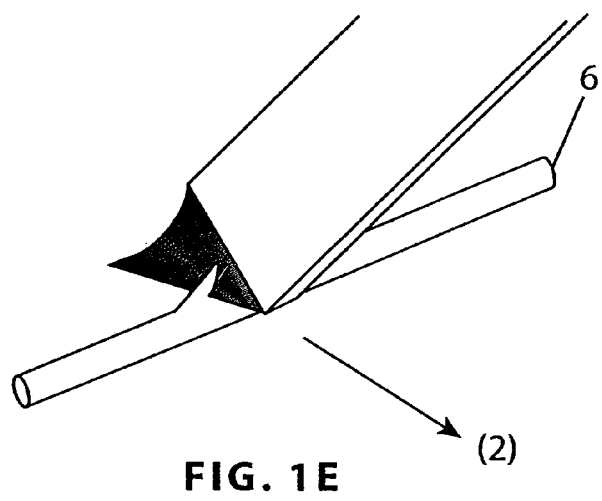
Figure 1F:
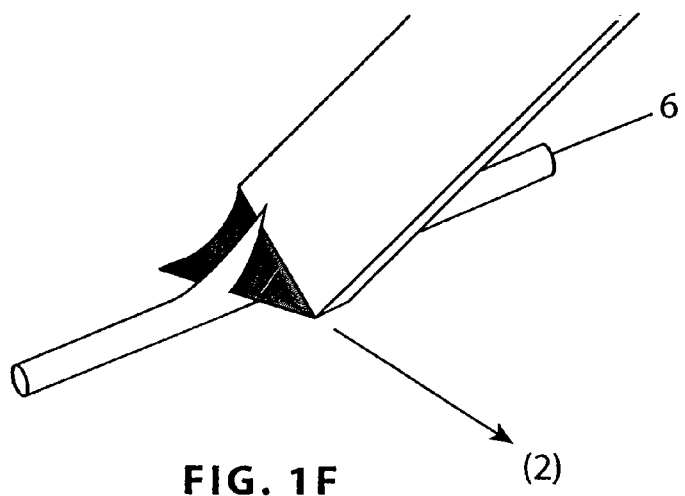

As shown in FIGS. 1E and 1F, this blade geometry allow a cut into suture 6 in the y and z directions during movement of blade 8 in direction (2). Comparison of FIG. 1E with FIG. 1F illustrates how movement of blade 8 in direction (2) increases the length and depth of the barb.

Figure 2A:
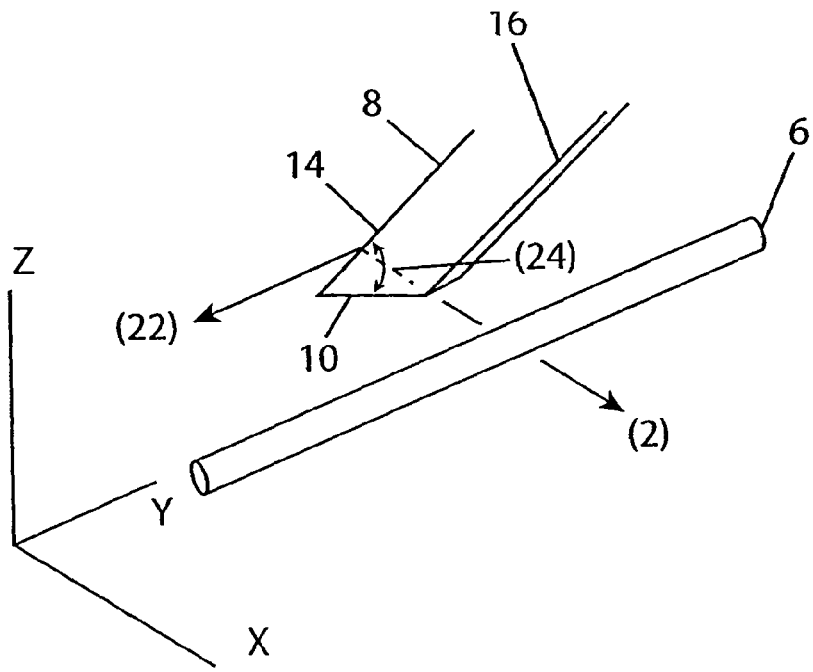
FIGS. 2A-C depict the cutting motion of a blade with two degrees of freedom from blade movement and one degree of freedom from blade geometry.
Figure 2B:
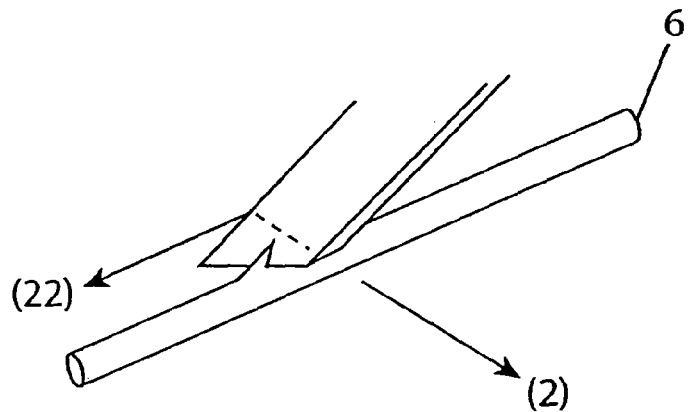
Figure 2C:
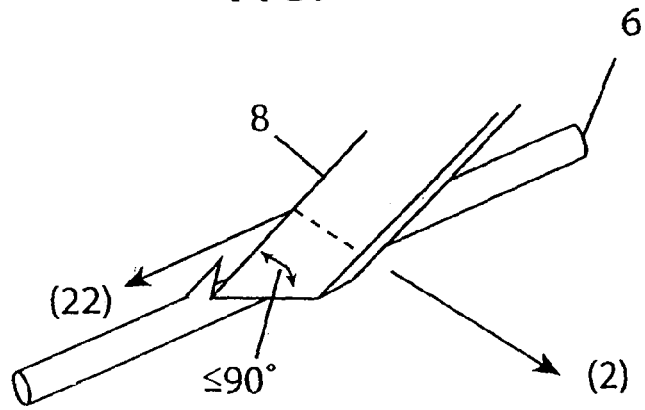

Turning now to FIGS. 2A-C, a consistent cutting motion of a blade with two degrees of freedom of movement and one degree of freedom from blade geometry is illustrated. Two degrees of freedom of movement is movement in two directions x and y. For FIG. 2A, direction (2) follows the lateral "x" axis and direction (22) follows the forward "y" axis in the cut of suture 6. In this regard the movement of blade 8 in two directions (2) and (22) simultaneously may be used to accomplish a cut. Edge 10 of blade 8 is at an angle of 90° or less, depicted as (24), of one degree in its blade geometry between the tips of sides 14, 16 of blade 8.

As shown in FIG. 2B, forward movement in direction (22) and along a lateral direction (2) allows a longer cut into suture 6 than produced in FIG. 1, since in FIG. 1 the blade geometry and blade movement in the x-axis determines the length of the barb, whereas in FIG. 2 the blade geometry and blade movement along both the "y" and "x" axes determines the length of the barb. This longer cutting action is in the "y" direction. FIG. 2C shows the completed cut of the suture 6 with a continued movement in direction (2) away from the suture.

Figure 3A:
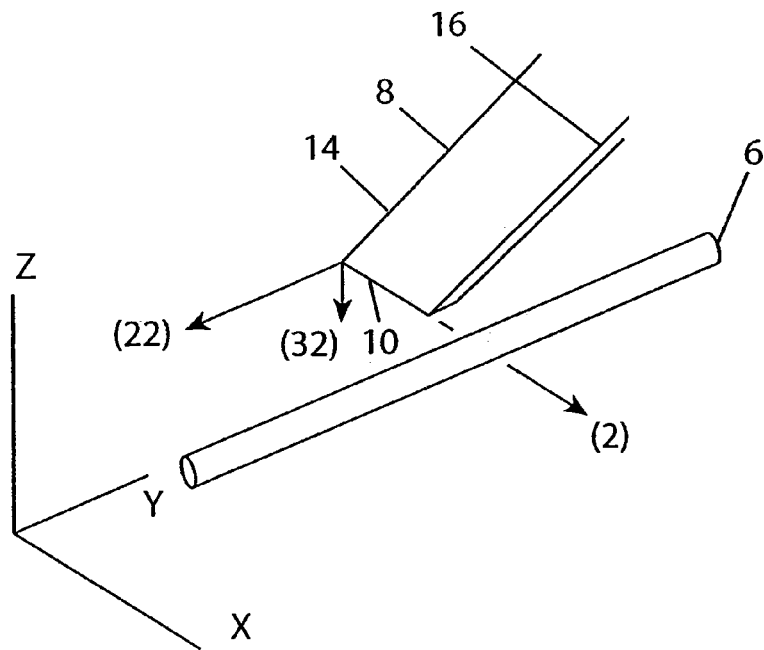
FIGS. 3A-C depict the cutting motion of a blade with three degrees of freedom from blade movement and a solid plane geometry.
Figure 3B:
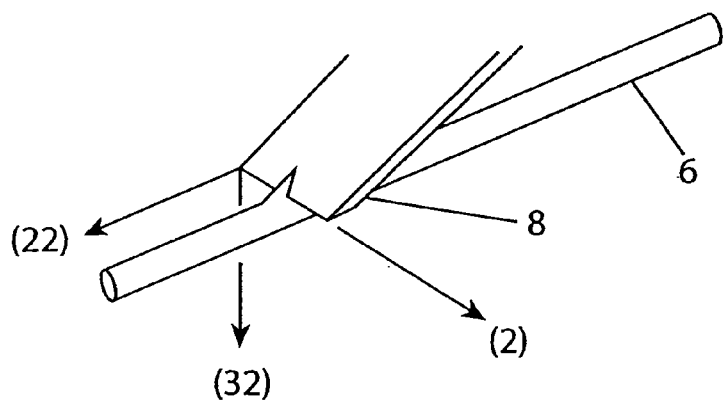

FIG. 3A illustrates a further consistent cutting motion of a blade with three degrees of freedom of blade movement and edge 10 of 90° or less. Three degrees of freedom from movement is movement in the three directions of a three-dimensional "x-y-z" layout. For FIG. 3A, direction (2) follows the lateral "x" axis, direction (22) follows the forward "y" axis and direction (32) follows the downward "z" axis. The movement of blade 8 in all three directions (2), (22) and (32) may be used to accomplish the cutting of a barb on the suture 6.

Figure 3C:
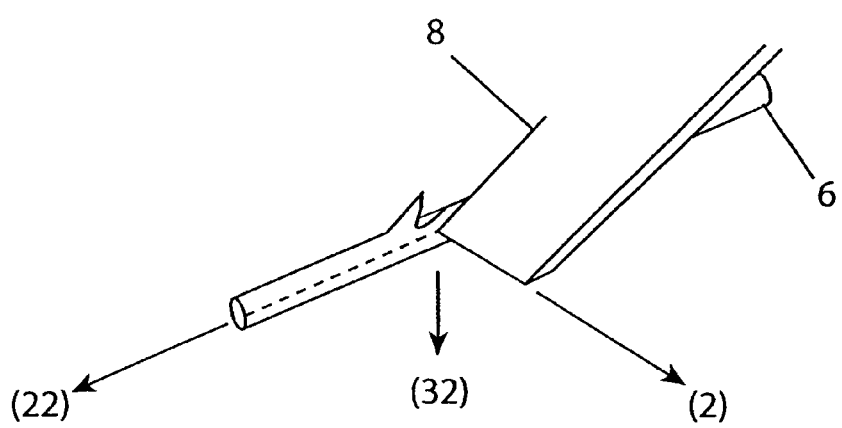

The combination of movement in lateral direction (2), forward direction (22) and downward direction (32) would allow one to vary the length and depth of the cut to create a barb. It may be a deeper barb by cutting further in direction (32) and/or a longer barb by cutting further in direction (22). By moving blade 8 in lateral direction (2), forward direction (22) and downward direction (32) simultaneously forms a trajectory, which may be altered to create barbs with different qualities such as aspect ratios. FIG. 3C shows the completed cut of suture 6 with a continued movement in directions (2), (22) and (32) away from the suture 6.

Figure 4A:
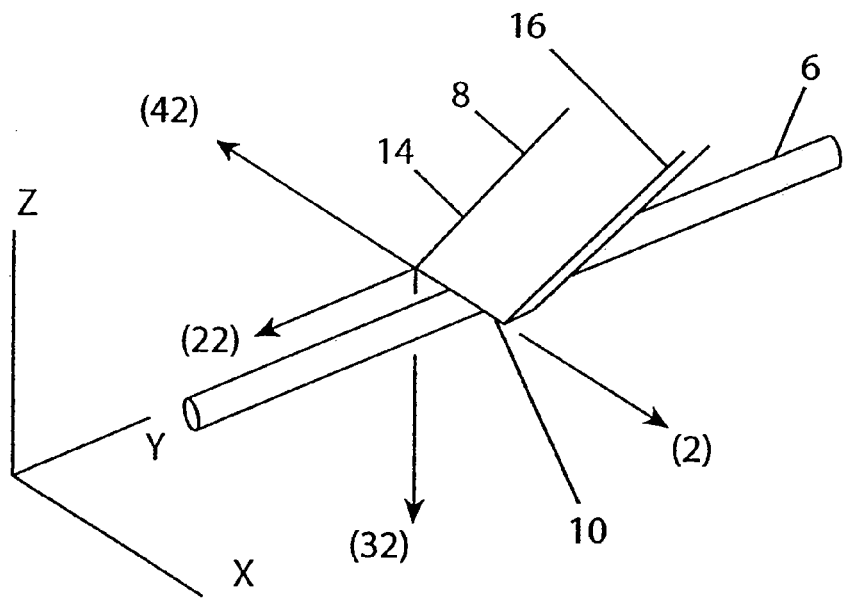
FIGS. 4A-C depict a zigzag (oscillating back and forth and downward) cutting motion of a blade with three degrees of freedom from blade movement and solid plane blade geometry.
Figure 4B:
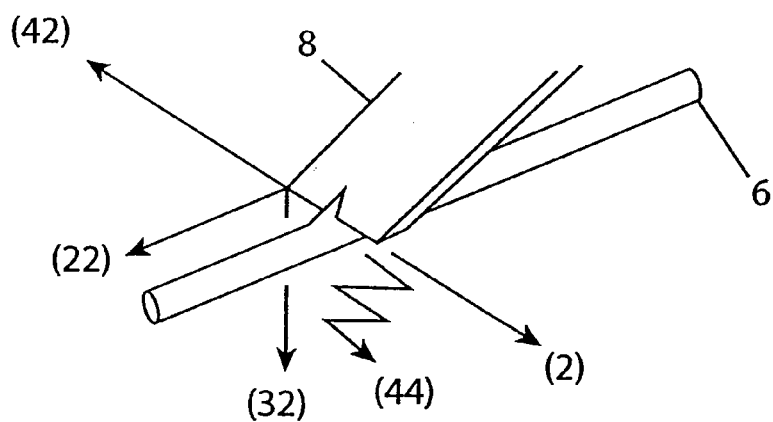
Figure 4C:
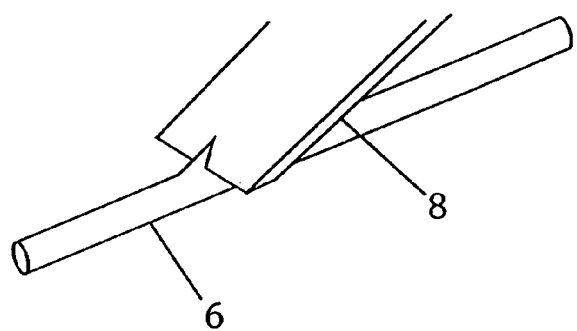

A yet further method of cutting a barb is shown in FIGS. 4A-C where a back and forth or zigzag (oscillating on the "x" axis combined with the movement in z and/or y axis) motion of the blade with three degrees of freedom of blade movement and a solid plane geometry cuts the barb with a saw-like cutting motion. Three degrees of freedom of movement is movement in three directions in the three-dimensional "x-y-z" layout. In FIG. 4A, direction (2) follows the lateral "x" axis, direction (22) follows the forward "y" axis, direction (32) follows the downward "z" axis, and direction 42 follows the lateral "x" axis except in a direction opposite to direction (2). FIG. 4A shows the movement which may be used to accomplish a cut of blade 8 in directions (22) and (32) with alternation in movement between directions (2) and (42). Edge 10 of blade 8 would be straight between the tips of sides 14, 16 of blade 8.

The combination of alternating movement in lateral directions (2) and (42), steady movement in forward direction (22) and steady movement in downward direction (32) allows the depth of the cut to be varied. The resultant zigzag cutting motion is shown as alternating direction (44) in FIG. 4B. FIG. 4C shows the completed cut of suture 6.

Figure 5A:
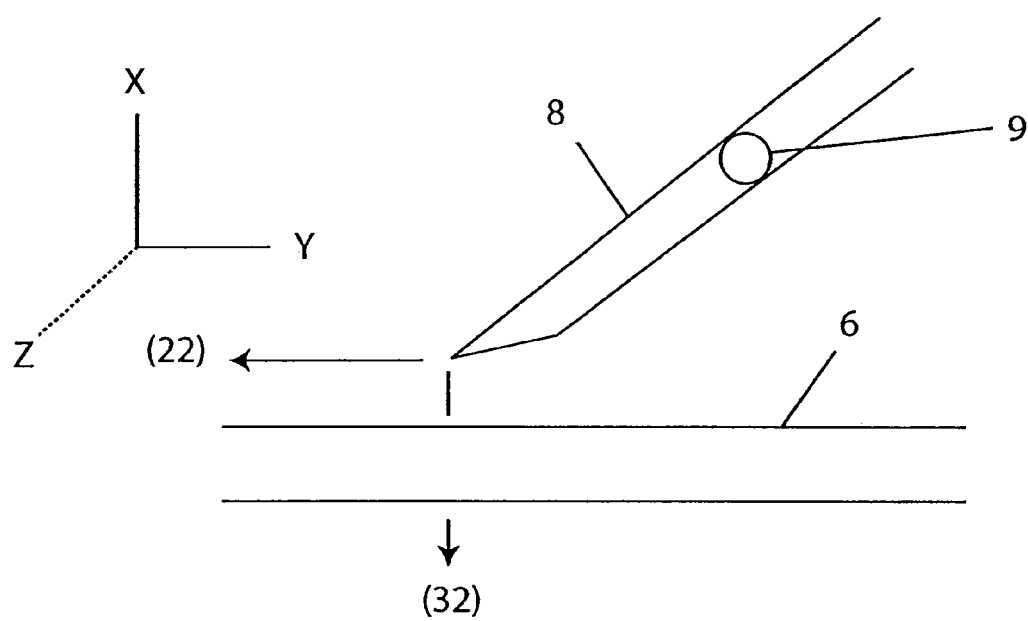
FIGS. 5A-C depict the cutting motion of an articulating blade with three degrees of freedom from blade movement.
Figure 5B:
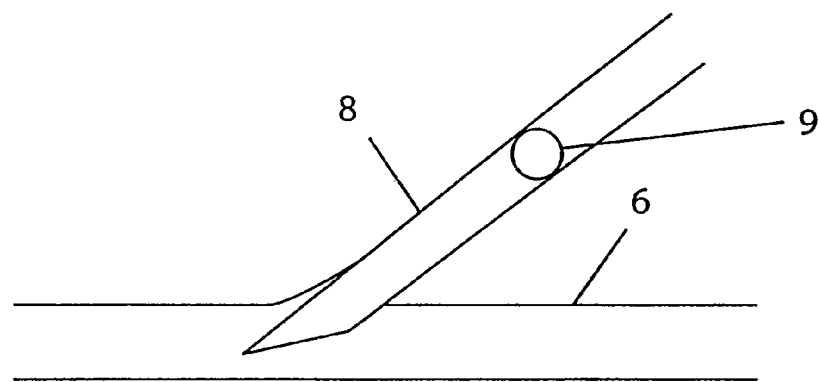
Figure 5C:
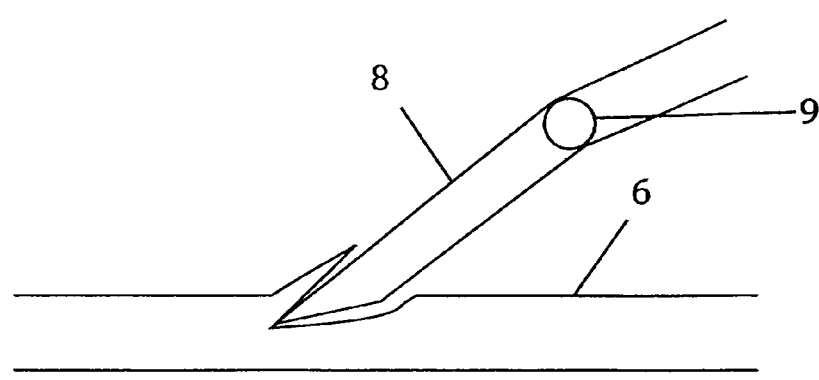

A still further method of cutting a barb is shown in FIGS. 5A-5C where articulation of blade 8 about an axis 9, in combination with any of the cutting motions described in FIGS. 1-4 above, may be used to vary the depth of the barb. In FIG. 5A, direction (2) follows the lateral "x" axis (into the plane of the drawing), direction (22) follows the forward "y" axis and direction (32) follows the downward "z" axis. FIG. 5B shows the blade movement which may be used to accomplish a cut of blade 8 in directions (2) and (22), similar to that depicted in FIG. 2B. Forward movement in direction (22) and along a lateral direction (2) produces a barb based on two degrees of freedom of blade movement. In FIG. 5C, blade 8 is also allowed to articulate about axis 9, providing an additional degree of freedom, which may be used to impart additional barb depth in direction (32) in the z-axis. This articulating motion of blade 8 may be employed in combination with any of the blade geometries and/or blade movements previously described. Articulation of blade 9 may also be used to lift a cut barb up and away from the surface of suture 6, thereby leading to a fuller or more pronounced barb.

The blade motion shown in FIGS. 1-5 can cut a suture filament made of polyglycolide, polydioxinone, polypropylene, other resorbables, other nonresorbables, Gore-Tex®, bi-component material or sutures made of other material suitable for the purpose.

While in the aforesaid examples, only a single blade is shown, it is envisioned that a plurality of blades may be utilized. They may be in tandem or on a rotary mechanism or on any other type of mechanical device which effects the implementation of the movement so described. Also, while the suture is shown in an untwisted state, it may be cut in a twisted state as hereinafter described.

By way of examples of mechanical devices for implementing the foregoing, reference is made to FIGS. 6-19 and 21-22. It should be understood, however, that these devices should not be considered exclusive and other types of devices for such implementation are contemplated.

Figure 6:
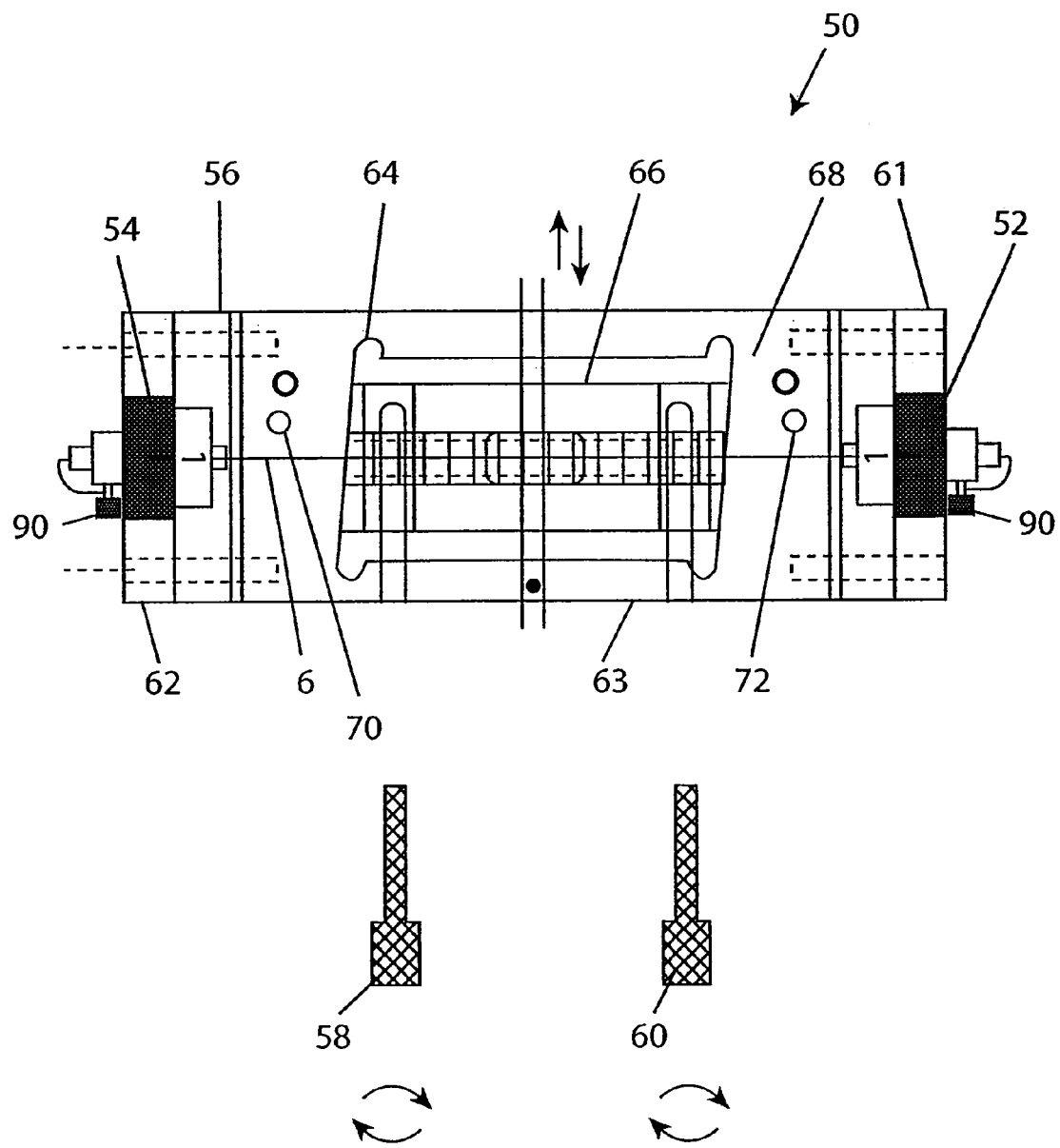
FIG. 6 is a top view of the assembled cutting device.
Figure 7:
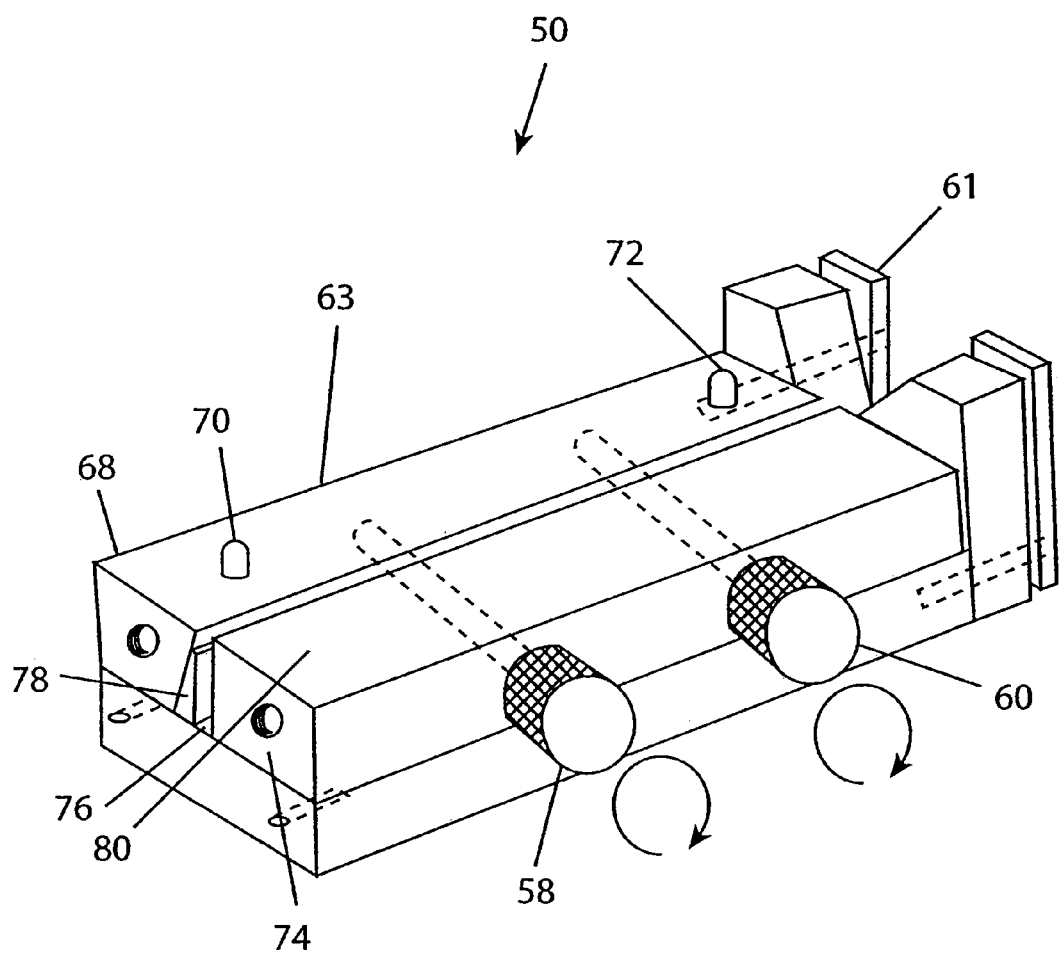
FIG. 7 is a perspective view of the cutting bed.

Turning now more particularly to FIG. 6, there is shown a cutting device 50 that allows an operator to cut multiple barbs on the exterior of suture 6 using the methods previously described. The cutting device 50 includes retention knobs 52, 54 for retaining the suture 6 on a vise 63 during cutting. Retention knobs 52, 54 include knob holders 61, 62. Cutting bed vise screws 58, 60 are used to open and to close cutting bed vise 63, where suture 6 is placed during cutting.

A cutting template 64 directs the cutting motion of a blade assembly 66 containing a plurality of blades across suture 6. Two additional cutting templates are provided for operation of the cutting device but are offset to provide a different axial position of the blades with respect to suture 6. The cutting templates have the same configuration as cutting template 64 and are installed in a similar manner throughout the several views. Also, while the templates shown are particularly suited for practicing one way of cutting the barbs, such templates can be readily modified to allow the performance of other ways, including those previously described as will be appreciated by a skilled artisan.

Cutting bed vise 63 assists in the alignment of the cutting templates. On the top of block 68 of cutting bed vise 63 are two protrusions. These protrusions are alignment pins 70, 72 which are used for setting the cutting templates and a tamp 101.

As will be apparent to one skilled in the art, the configuration of cutting bed vise 63 may vary. If the suture is rotated (e.g. 120 degrees or 180 degrees) to effect cutting barbs about its circumference, the cutting bed vise may be configured as shown in FIG. 6. If the suture is twisted prior to cutting, as will be discussed, the cutting bed vise 63 preferably has a configuration with trapezoidal sides such as those shown in FIG. 7. Because suture material is somewhat compliant, this design provides superior clamping to a vise with parallel sides. Note that the vise shown in FIG. 7 can also be used with a rotated suture, since there is a space to accommodate a cut barb. In this regard, in FIG. 7, blocks 68, 74 taper outward from the tops on their interior sides to a surface 76, with the blocks depicting a trapezoidal shape when viewed from an end profile. Protruding from the taper of block 68 is a trapezoidal or anvil suture clamp 78 which is used to secure suture 6 during the closing of cutting bed vise 63. Suture clamp 78 is a wedge shape which sets on surface 76 and ends slightly below top 80.

Figure 8:
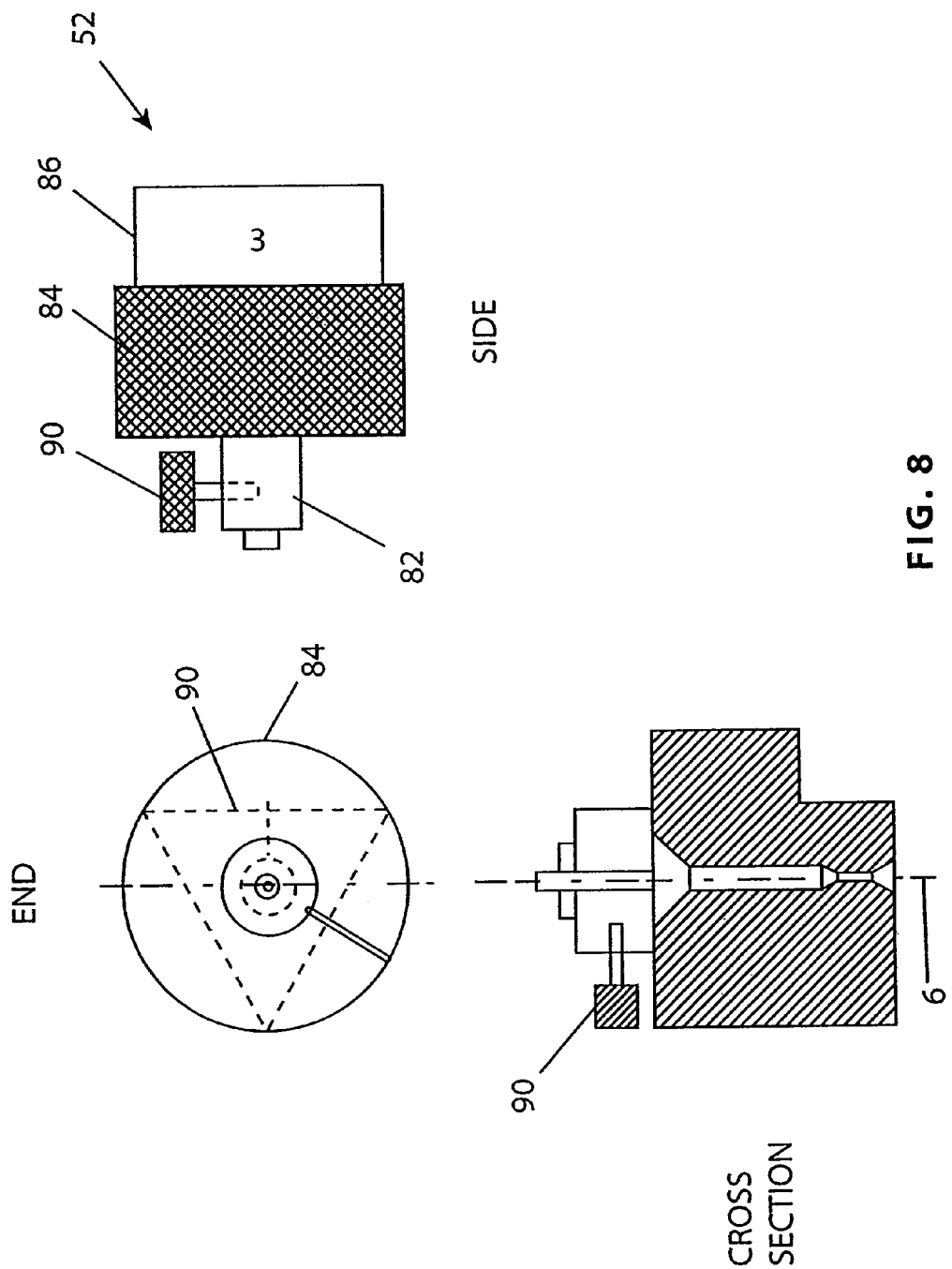
FIG. 8 depicts an end, a side, and a cross-sectional view of the retention knob of the cutting device.

In addition to securing suture 6, retention knobs 52, 54 are rotated between the various cutting methods and are numerically indexed for precise movement. As depicted in FIG. 8, retention knob 52 is a solid elongated body. Retention knob 52 comprises a cylinder 82 having a gripping area 84 integral with a triangular protrusion 86. Triangular protrusion 86 can rest on cutting bed 56 or a spacing bar 100, shown in FIG. 13. An anchor screw 90 secures suture 6 to the retention knob. The triangular protrusion includes numerical marks for guiding the operator in positioning the retention knob during various stages of the cutting method; however, the triangular protrusion may be indexed in other variations. One side of the triangular protrusion has the number "1" imprinted, another side has the number "2" imprinted and a third side has the number "3" imprinted. Retention knob 54 has the same characteristics as retention knob 52.

Figure 9:
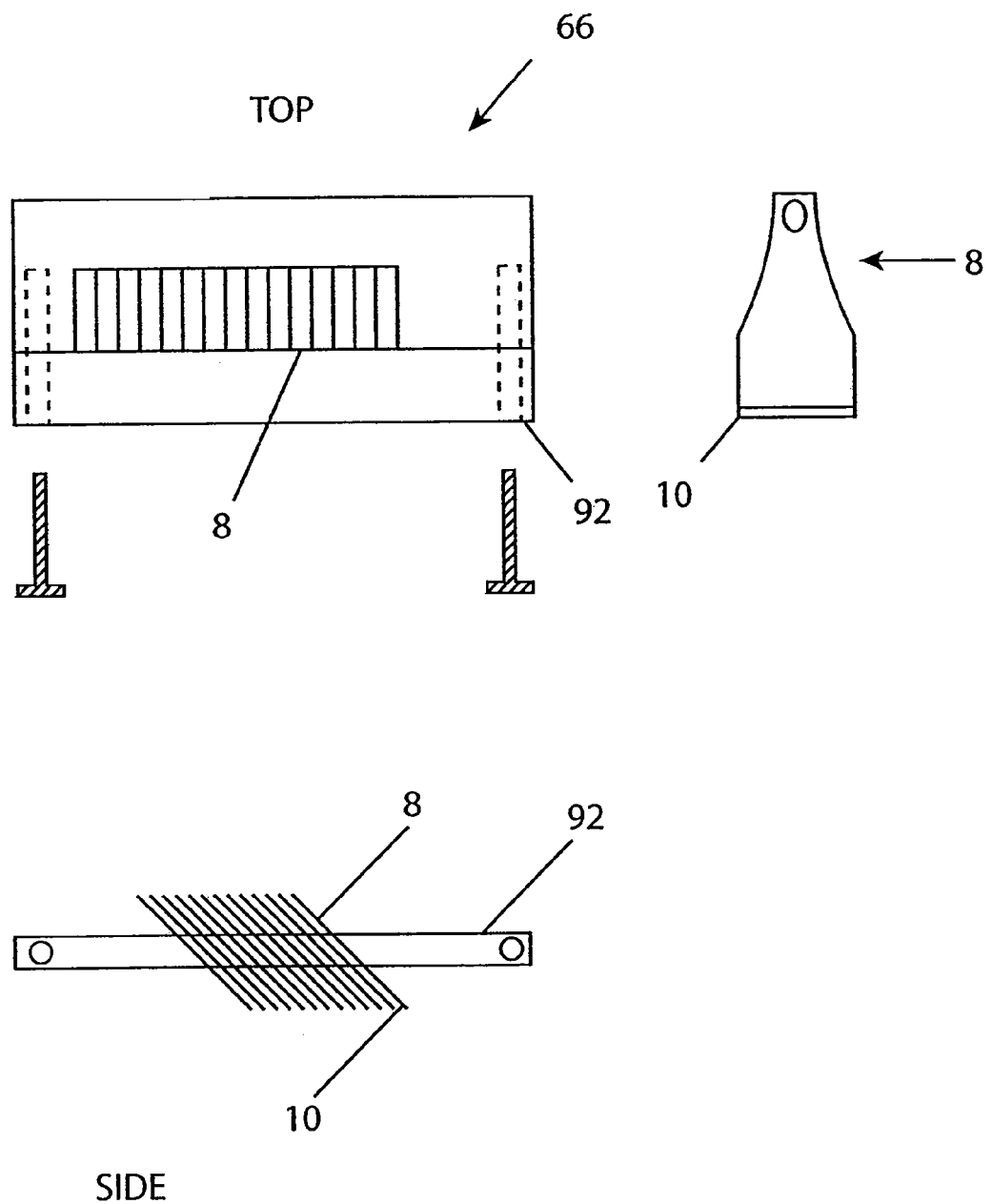
FIG. 9 depicts a top and side view of the blade assembly of the cutting device and a top view of an example blade for the blade assembly.
Figure 10:
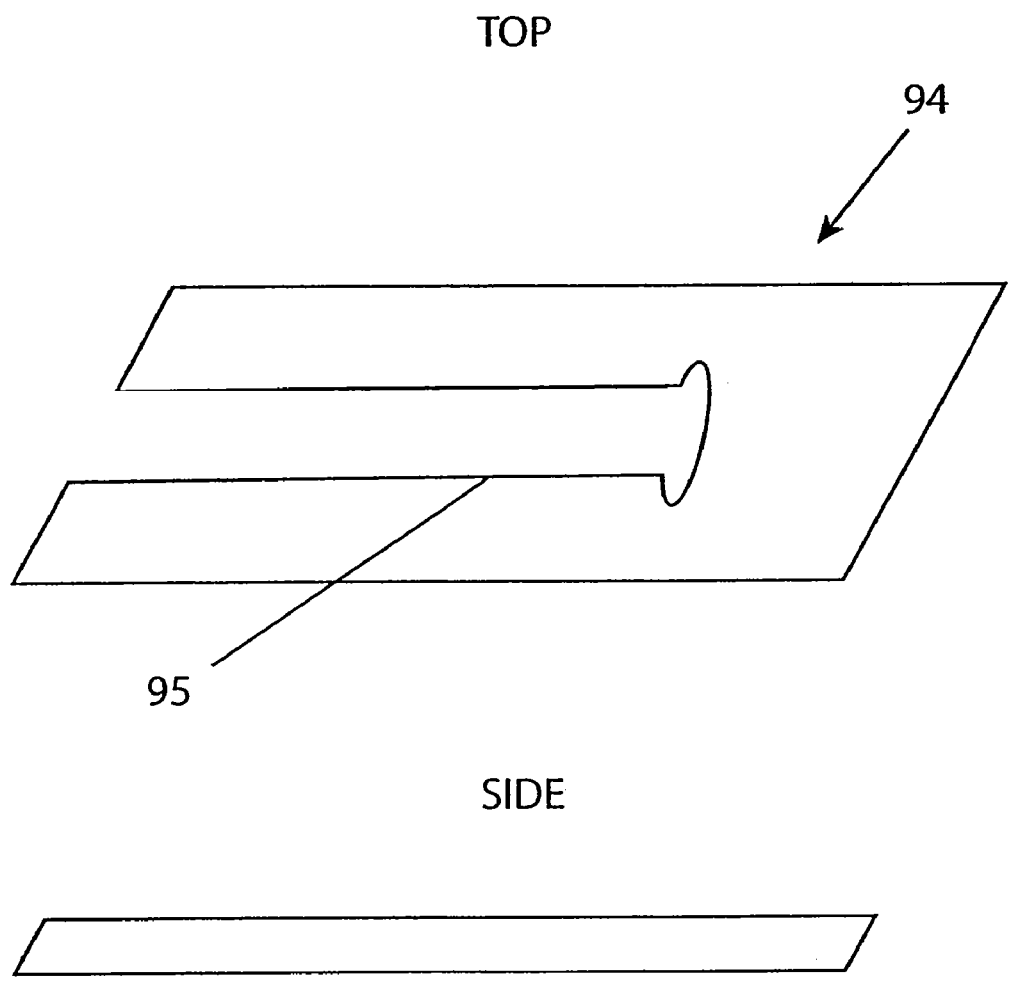
FIG. 10 depicts a top and side view of the template block of the blade assembly.

For cutting a plurality of barbed sutures at one time, a multi-blade assembly is used. As depicted in FIG. 9, blade assembly 66 consists of a plurality of blades 8 secured in retaining block 92. In FIG. 8, thirteen blades are depicted, although obviously the number of blades used may vary. Edge 10 of each of the blades used in the blade assembly 66 would extend through a template block 94, shown in FIG. 10 by the amount of the desired barb depth.

Retaining block 92 of FIG. 9 consists of two rectangular blocks which retain blade assembly 66 by a vise action. Blade assembly 66 conformingly fits to a cutaway section of the retaining block and blades 8 are inserted at a desired angle, which in this case is 148 degrees. The blades are secured in the retaining block 92 with the template block 94 attached thereto. Template block 94 acts as a guide for the blade assembly within the confines of the cutting templates.

Figure 11:
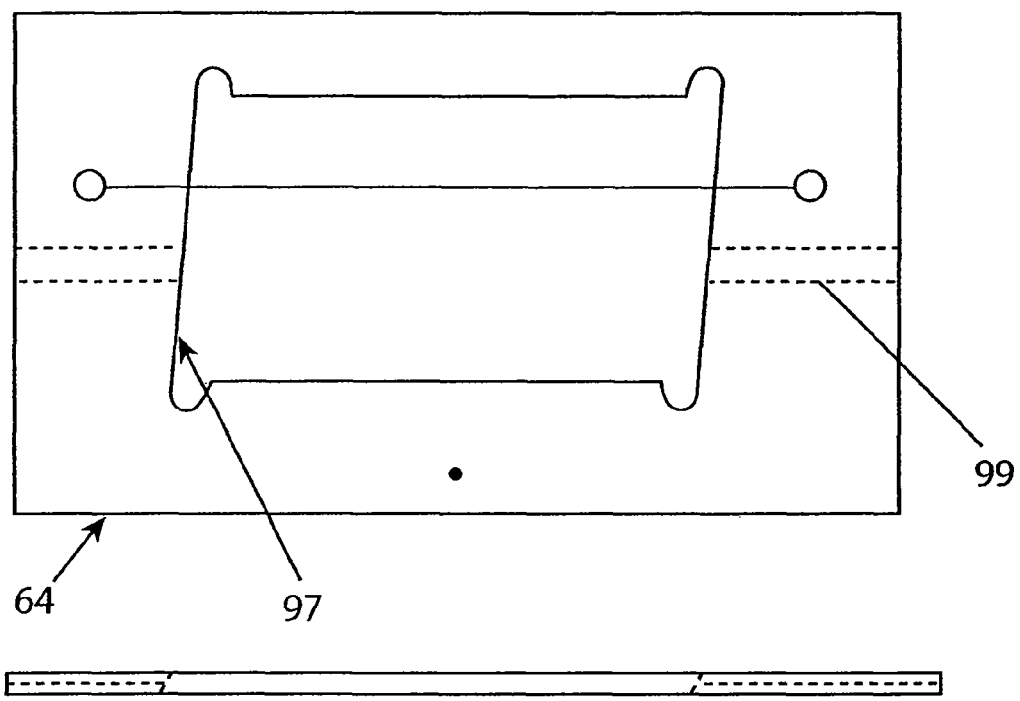
FIG. 11 depicts a top and side view of the cutting template used with the cutting device.

As shown in FIG. 11, the cutting template 64 provides a cutting path 97 for blade assembly 66. Cutting path 97 is shown as a parallelogram perimeter. Note, however, for example, the cutting path 97 may be shaped with a rectangular perimeter to suit the movements described in the cutting method of FIG. 1, or other shapes to permit additional degrees of blade movement as described in FIGS. 2-5. Additional cutting templates are provided and are similarly made with the purpose of offsetting the blade cut in an axial direction. The cutting template 64 is identified so as to indicate to the user which one is to be used at which stage of cutting. On opposite sides of the cutting template 64 is a channel 99 sized to accommodate the other sections of suture 6 not being cut by blade assembly 66.

Figure 12A:
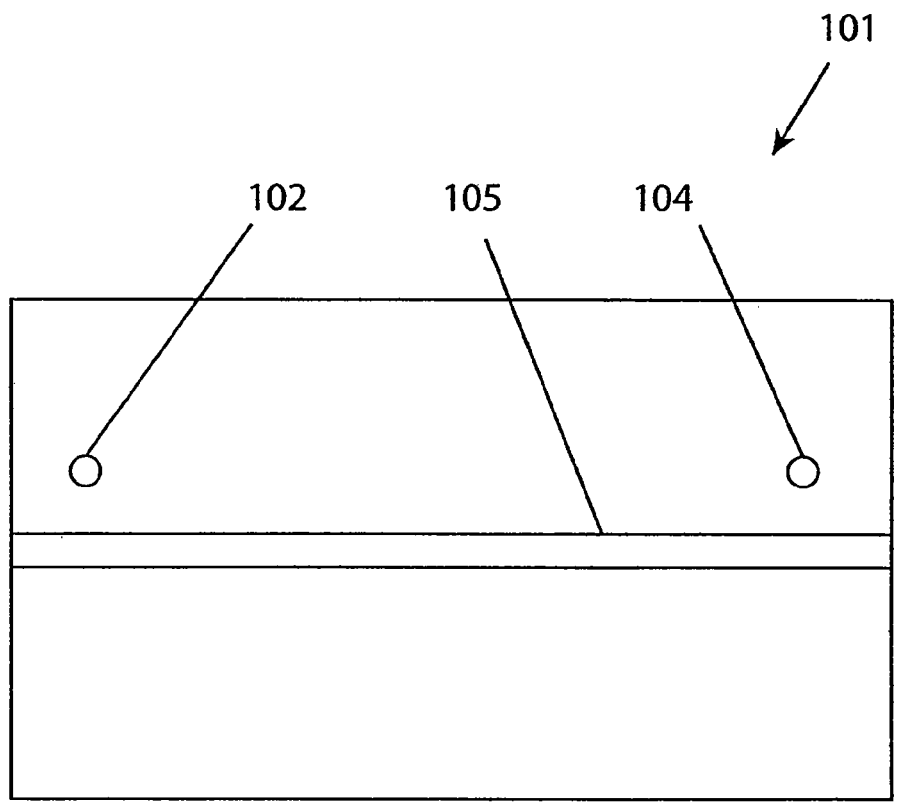
FIG. 12 depicts a top and side view of the tamp used with the cutting device.
Figure 12B:
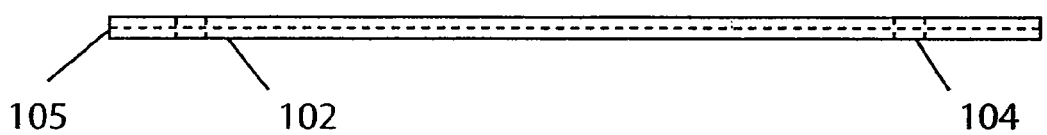

As shown in FIG. 12A, a tamp 101 is provided to insure that suture 6 is uniformly seated on the anvil 78. Apertures 102, 104 on tamp 101 are provided to engage the alignment pins 70, 72. A channel 105 is provided to hold suture 6 in place during the calibration. The depth of the channel 105 equals the thickness of the suture 6 above vise top 80.

Figure 13:
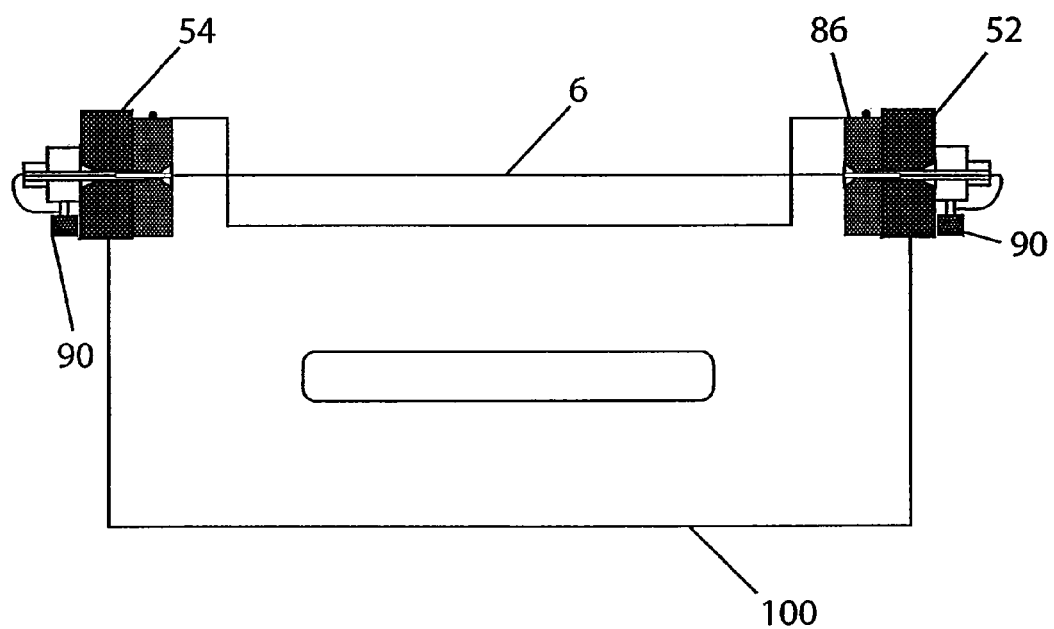
FIG. 13 depicts the securing of the suture to the retention knob and placement on the spacing bar.

To operate cutting device 50, first one secures the suture 6 to anchor screws 90 on one of retention knobs 52, 54 as shown in FIG. 13. Retention knob 52 is placed on the ledge of spacing bar 100 with the suture 6 drawn thereacross with the second retention knob 54 positioned on the opposing ledge. The suture should not be overly taut once it is secured to the second retention knob by anchor screw 90. After sizing, suture 6 is placed on cutting bed 56 and held in place by cutting bed vise 63. The retention knobs 52 and 54 are indexed in a first position. As will be apparent in a second and third cutting for a barbed suture having barbs spaced 120 degrees apart, retention knobs 52 and 54 are rotated to second and third positions respectively.

Figure 14:
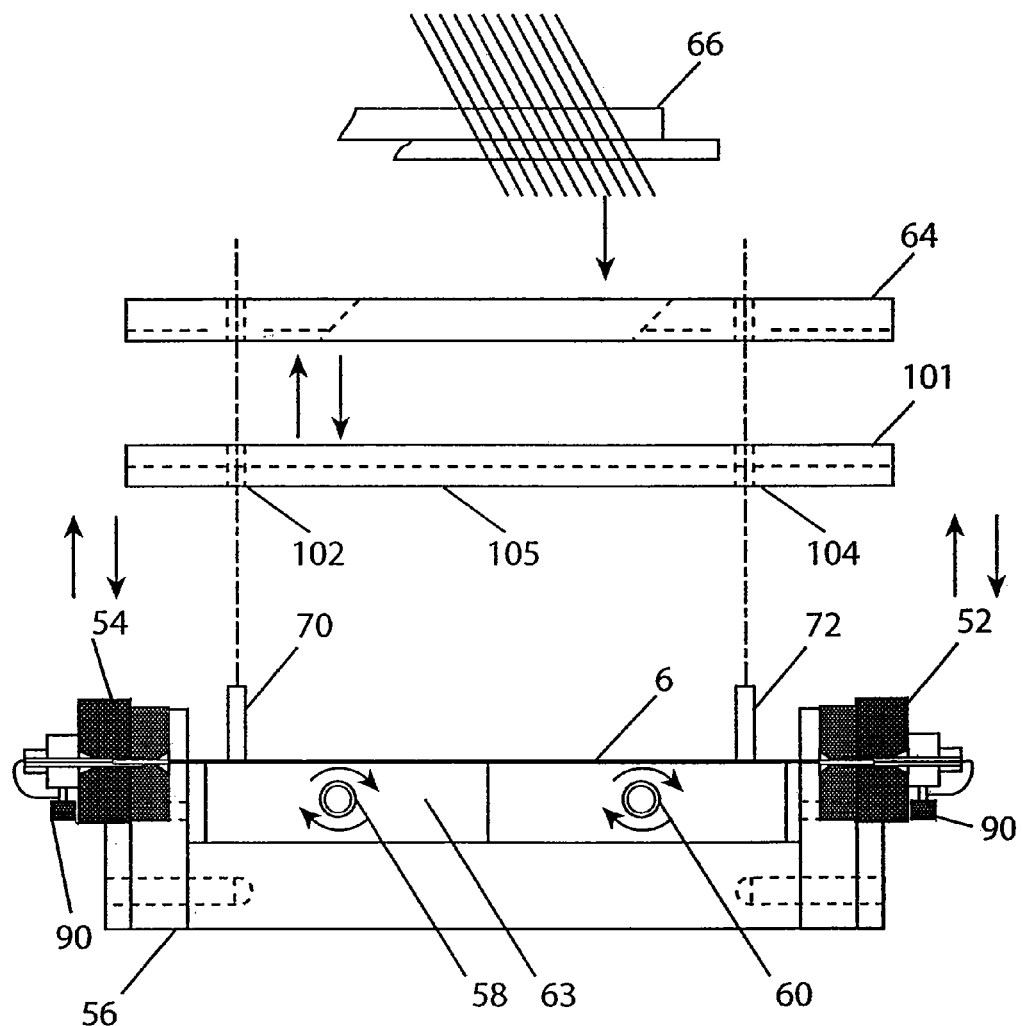
FIG. 14 depicts the placement of the various fixtures used with the cutting bed vise.

As shown in FIG. 14, the tamp 101 is placed on the cutting bed 56 positioning the suture 6 in vice 63 which is tightened, and the tamp is then removed. Cutting template 64 is then placed onto cutting bed 56.

Figure 15:
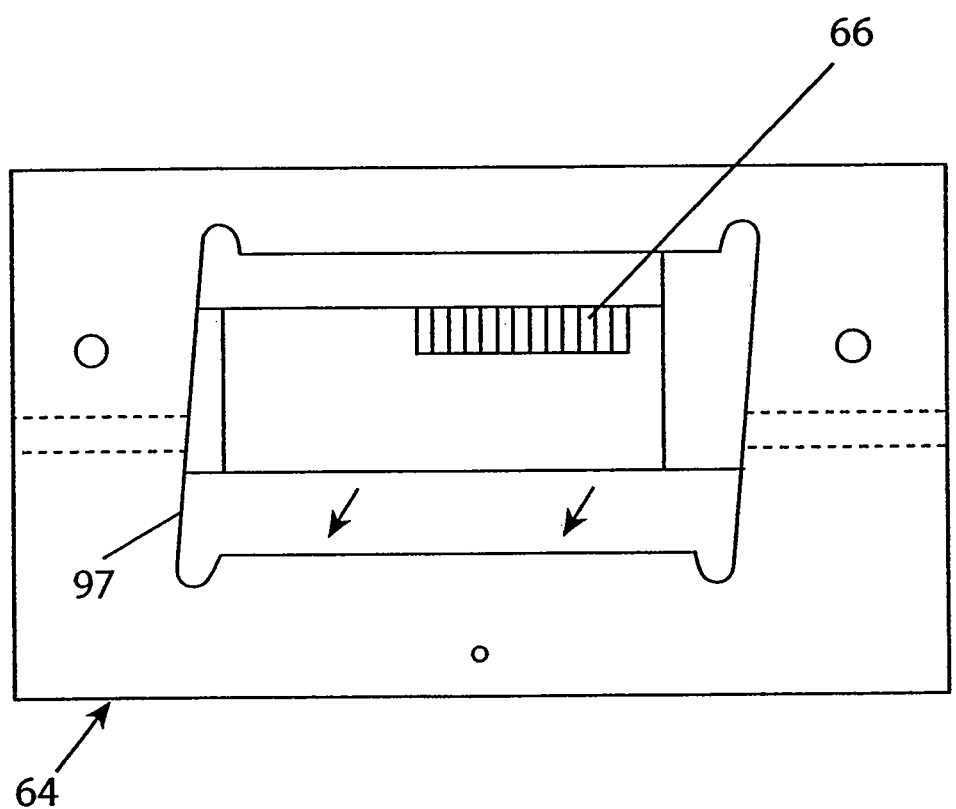
FIG. 15 depicts the blade assembly placement and downward movement in relation to the cutting template with the rest of the cutting device removed from the figure for clarity purposes.
Figure 16:
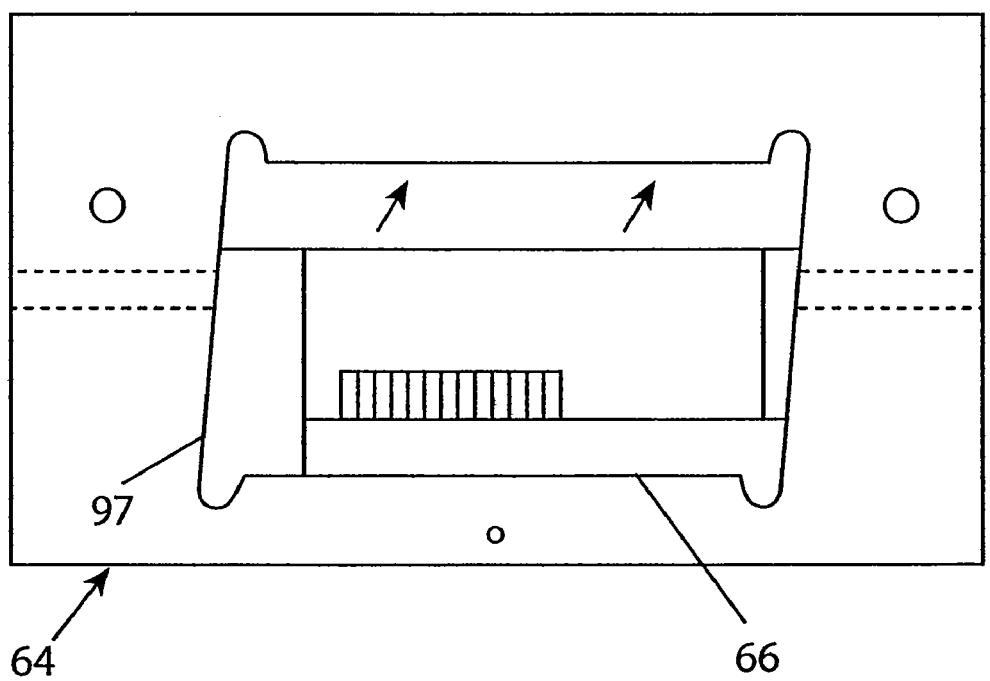
FIG. 16 depicts the blade assembly placement and upward movement in relation to the cutting template.

In the cutting method of suture 6, blade assembly 66 is placed onto cutting bed 56. The blade assembly is pressed down while slid from the top of the cutting template to the bottom along path 97 as shown in FIG. 15. The blade depth is set to produce the desired depth of the barb. After blade assembly 66 stops at the bottom of cutting template 64, the blade assembly is removed. To create barbs in a direction opposite those first cut, blade assembly 66 may then be turned 180 degrees and placed onto cutting bed 56 as shown in FIG. 16. The left and top of the blade assembly are in contact with the right and bottom of the cutting template along path 97. The blade assembly is pressed down while the blade assembly is slid from the bottom to the top. After the blade assembly 66 stops at the top of cutting template 64, the blade assembly and the template are removed.

As the process proceeds, suture 6 may be rotated, e.g. 120 degrees, 180 degrees, etc., and the cutting process repeated as shown in FIGS. 15-16. The suture should be set securely in the opening of cutting bed vise 63 and previously cut barbs should not project above top surface 80, and the process is repeated. For three sets of barbs about the circumference, the suture is rotated three times, for two sets, two times, etc.

Figure 17A:
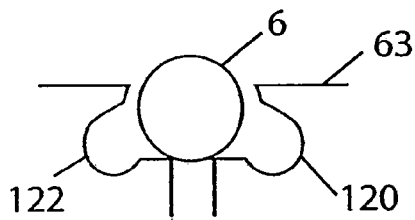
FIGS. 17A-F is a front view depicting the setting of barbs in the cutting bed vise before and after cutting using the 120 degree rotation method of cutting.
Figure 17B:
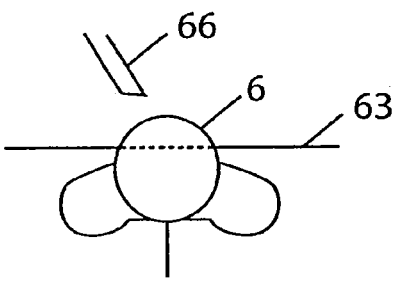
Figure 17C:
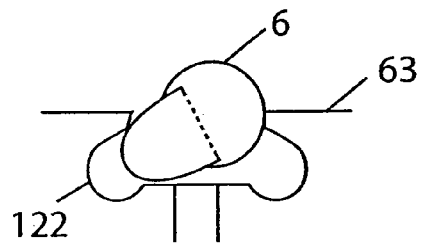
Figure 17D:
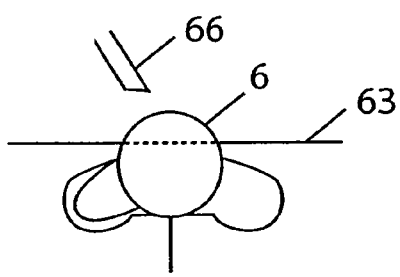
Figure 17E:
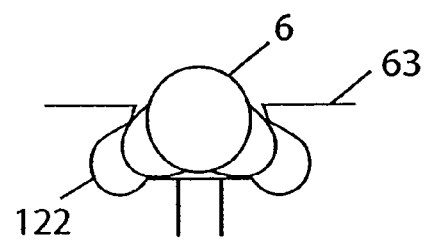
Figure 17F:
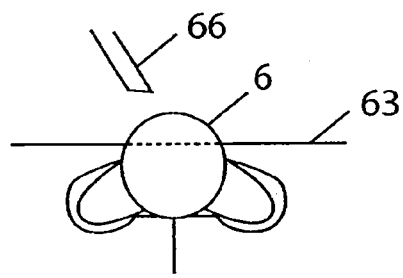

FIG. 17A-F shows the setting of the barbs in vise 63 before and after cutting for a suture having barbs spaced 120 degrees apart. FIG. 17A shows the vise open, suture 6 uncut, with vise notches 120, 122 unused. FIG. 17B shows the vise closed with blade assembly 66 about to cut suture 6. FIG. 17C shows the vise opened after the first set of barbs are cut and placed in notch 122. FIG. 17D shows the vise closed before blade assembly 66 engages suture 6 to cut the second set of barbs. FIG. 17E shows the vise open with two sets of barbs shown and placed in notches 120, 122. FIG. 17F shows the vise closed before blade assembly 66 engages suture element 6 for the cut. After cutting, the suture 6 is removed and examined. As will be apparent to a skilled artisan, additional or fewer notches may be provided for protecting barbs during subsequent cutting steps.

In the twisting method of cutting barbs, suture 6 is set up as previously described and twisted along its axis. The number of twists required are dependant upon the number of barbs, the material of the suture and the diameter of the suture. For example, it has been found that size 0, PDS-2 material requiring 2½" of barbs would require twisting it thirty-nine times for an acceptable result. Of course, too much twisting may cause the suture material to overrun itself, leading to undesirable results including damaged suture material.

Figure 18A:
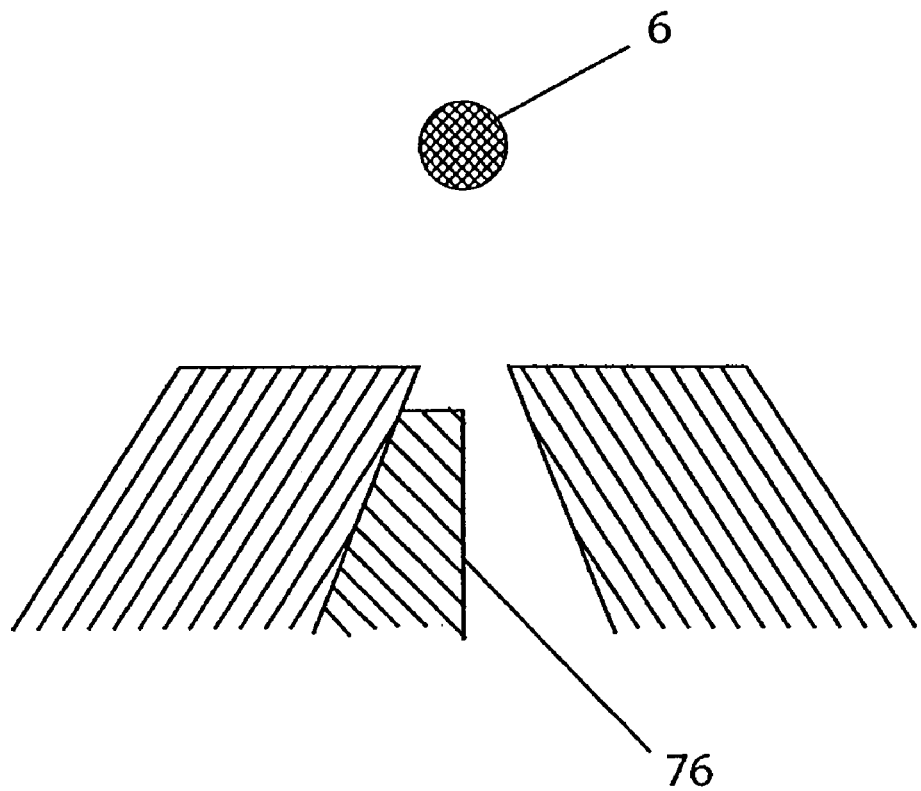
FIGS. 18A,B is a front view depicting the setting of the suture in the cutting bed vise before cut using the twisting method of cutting.
Figure 18B:
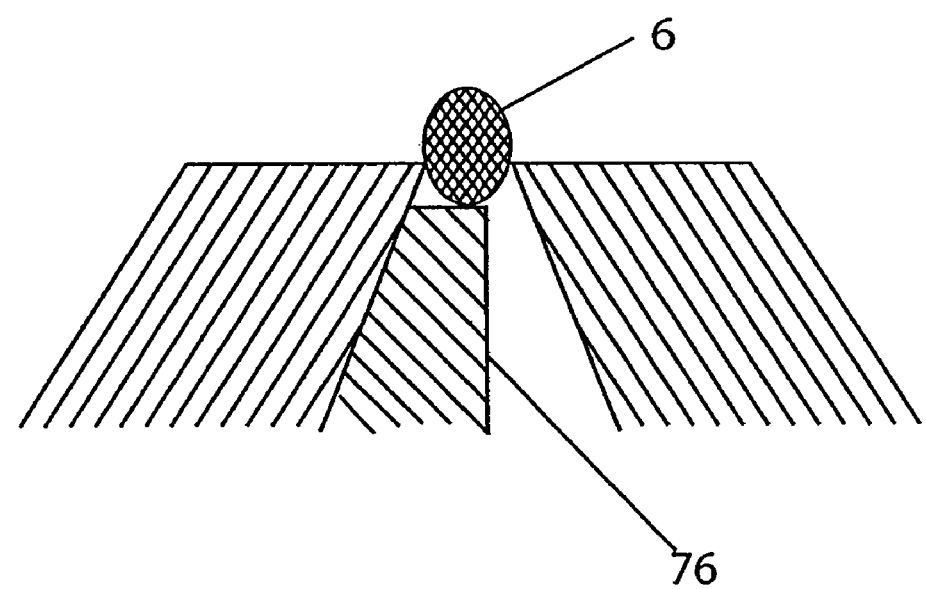

The securing of a twisted suture 6 on cutting bed 56 is, however, slightly different. In this regard, FIGS. 18A and B show the setting of suture 6 in clamp 76 before and during cut. FIG. 18A shows suture 6 being placed in the vise prior to clamping, with FIG. 18B showing the suture post clamping. The lightly clamped suture 6 forms an elliptical shape and is ready to be cut. The cutting method of suture 6 would be the same as that aforediscussed without, however, the need for the suture to be rotated.

Figure 19A:
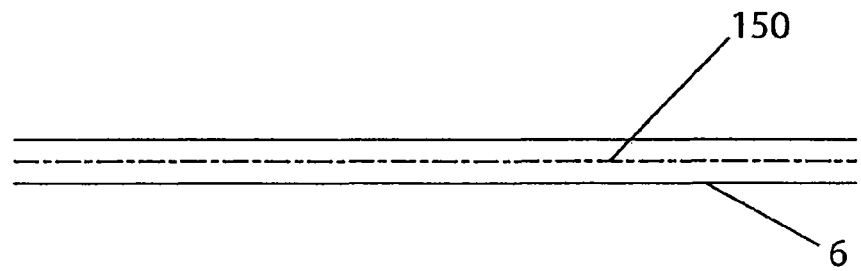
FIGS. 19A-D depicts the various conditions of a suture before and after the twisting method of cutting.
Figure 19B:
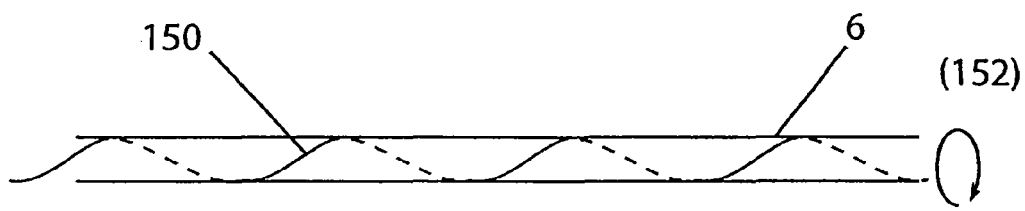
Figure 19C:
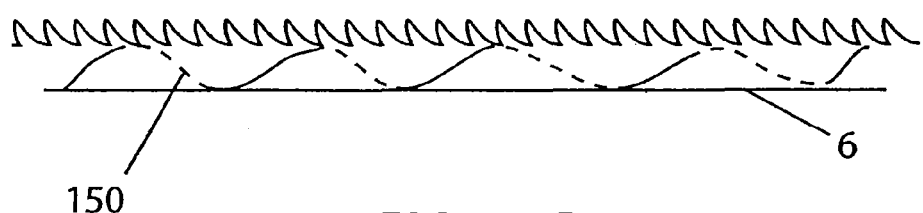

FIGS. 19A-D show the various conditions of suture 6 using the twisting method of cutting. In FIG. 19A the suture 6 is shown unmodified, with an imaginary line 150 shown to depict its longitudinal axis. FIG. 19B shows the suture 6 as it is twisted in direction (152) in preparation for cutting. FIG. 19C shows barbs cut in the twisted condition, with barbs cut along one side thereof. After the suture 6 has been cut and allowed to return to its untwisted condition, the barbs are such as those shown in FIG. 19D where the barbs spiral around the circumference of the suture.

Figure 19D:
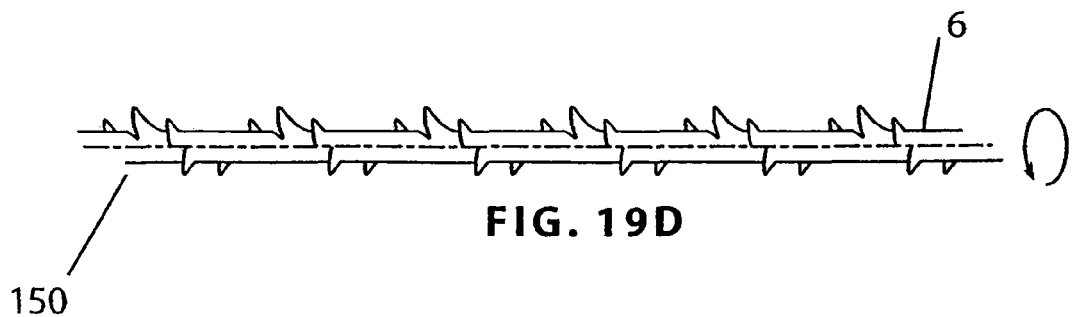
Figure 20:
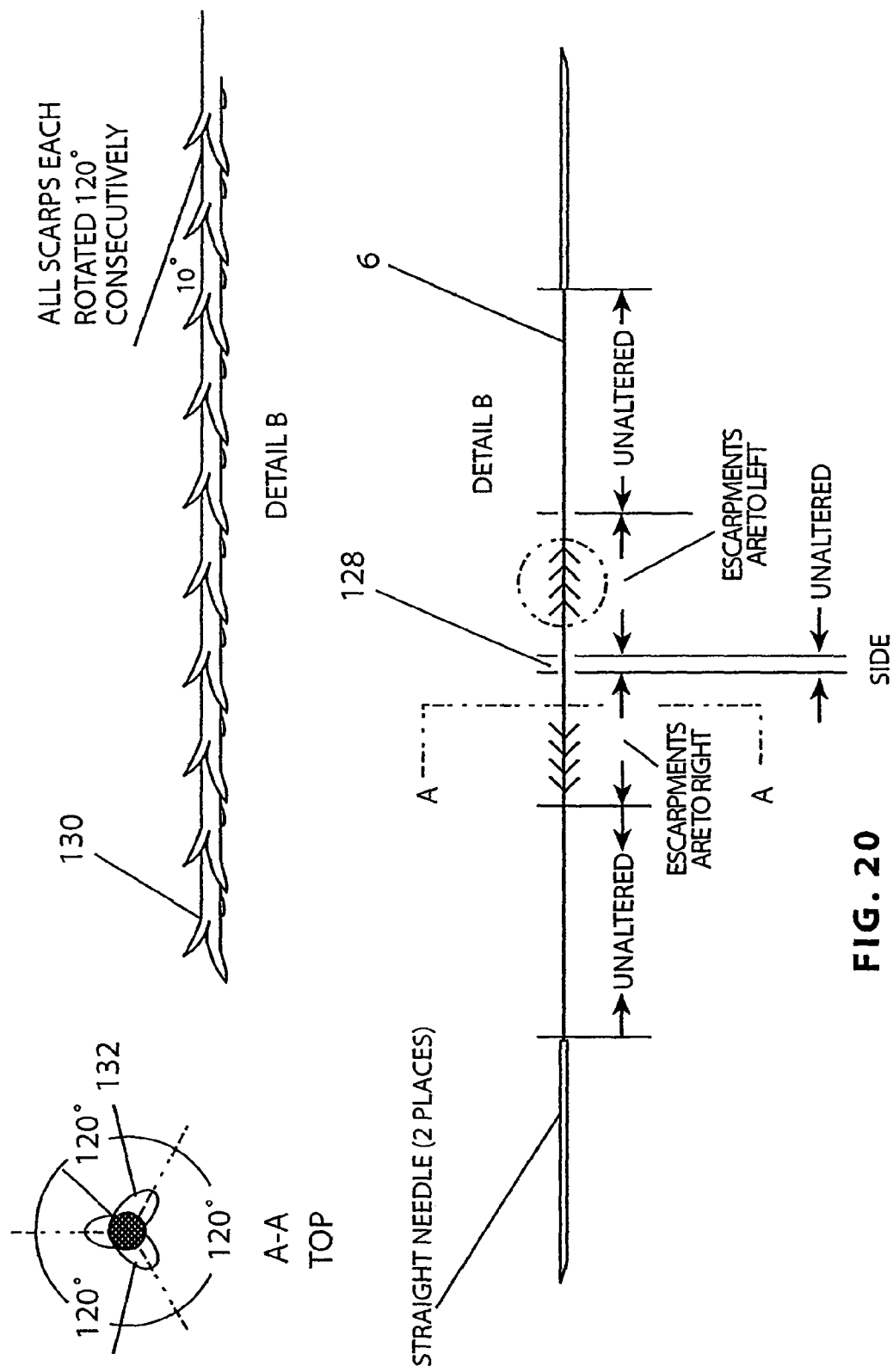
FIG. 20 is a side, top and detail view of a barbed suture using the 120 degree rotation method of cutting.

The difference in the placement of the barbs in the twisted versus the untwisted method can best be seen by comparing FIG. 19D with FIG. 20. In FIG. 20, the suture 6 cut in the untwisted state is shown with spaced barbs at 120° about the circumference of the suture 6. In FIG. 19D, the suture 6 was cut in the twisted state, and, upon de-twisting, the pattern of the barbs takes on a spiral configuration along the length of the suture 6.

Note that by omitting cutting motions when suture 6 is cut in either a twisted or untwisted state, the barbs can be formed in a random configuration on the exterior of the suture. Also, the suture may be cut in both a twisted and untwisted state to produce other types of random configurations of barbs.

Figure 21A:
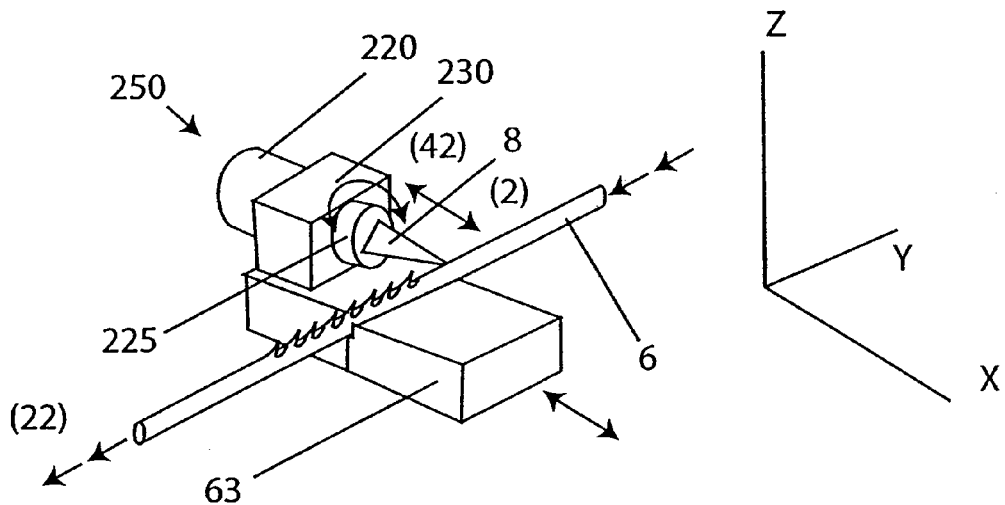
FIGS. 21A-C depict perspective views of a linear indexing mechanism with a rotary reciprocating blade assembly.
Figure 21B:
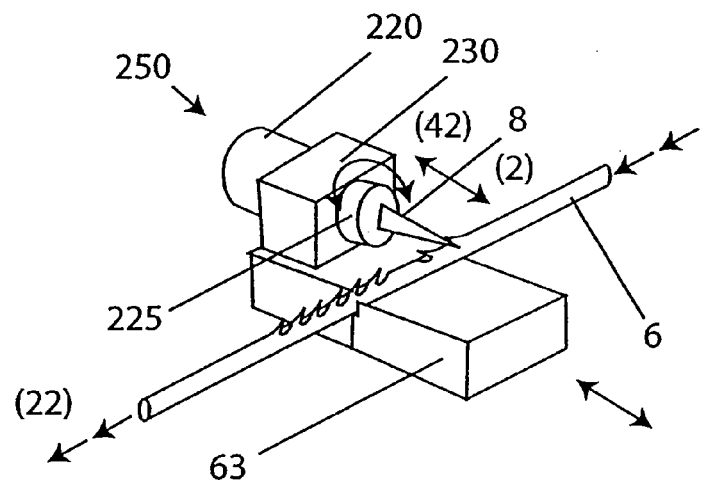
Figure 21C:
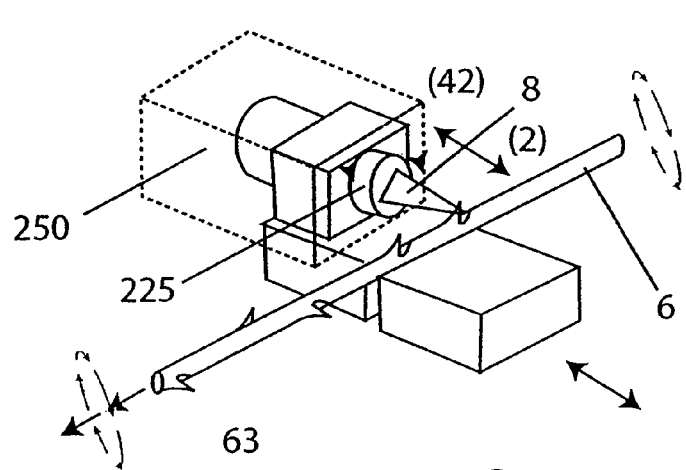
Figure 22:
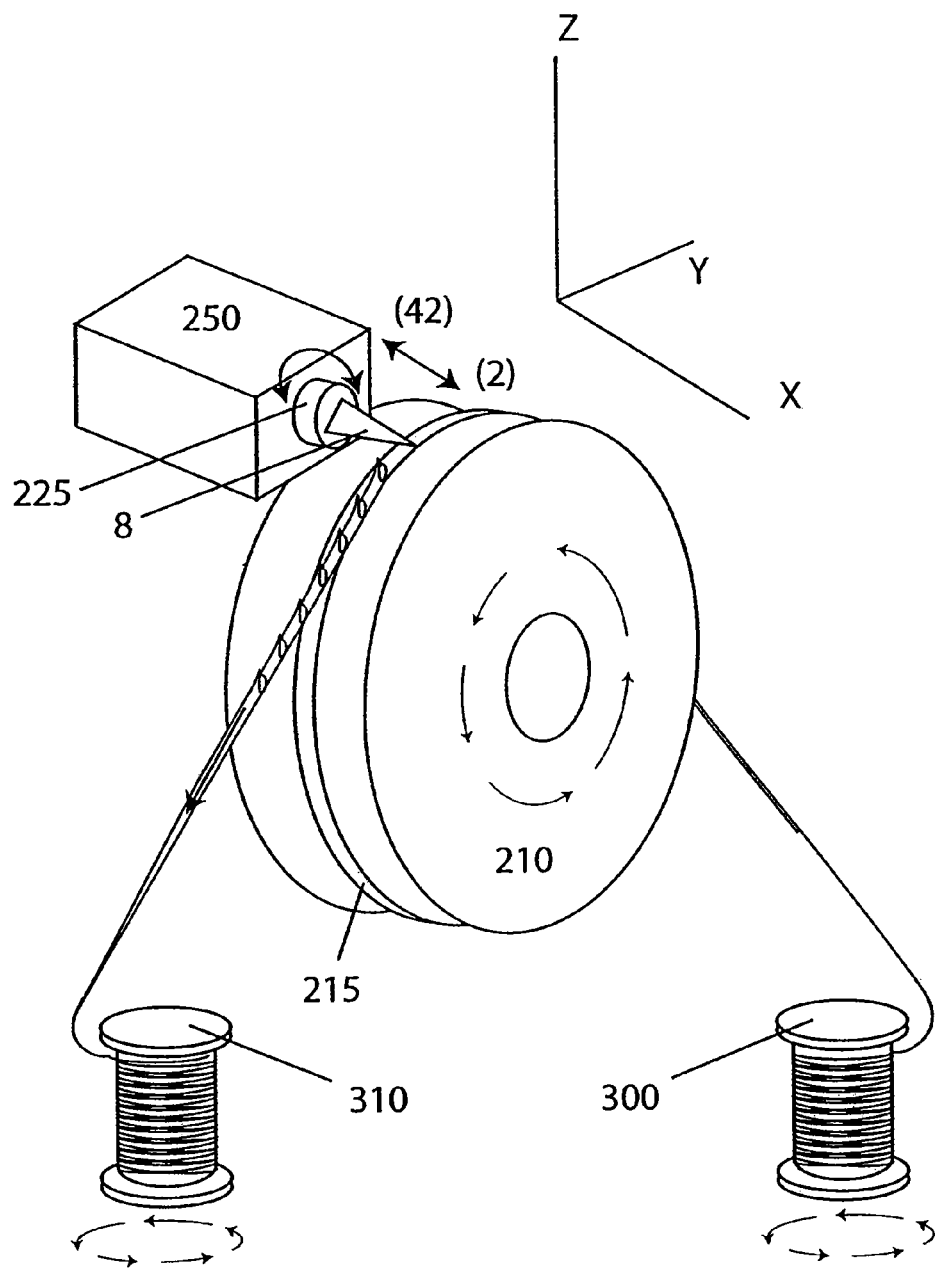
FIG. 22 is a perspective view of a rotational indexing mechanism with a rotary reciprocating blade assembly.

Alternate embodiments for cutting barbs according to the present invention are shown in FIGS. 21-22. FIGS. 21A-C show a linear indexing mechanism for advancing suture 6 along cutting bed vise 63 in direction (22), while reciprocating blade assembly 250 cuts barbs along the axis of suture 6. Suture 6 may be advanced along cutting bed vise 63 in a twisted state to form spiral cut barbs as shown in FIGS. 21A and B, in an untwisted state, or rotated about its axis in increments (e.g. 120 degrees, 180 degrees, etc.) as it advances as shown in FIG. 21C.

Reciprocating blade assembly 250 includes blade 8 connected via arm 225 to a linear reciprocating solenoid 220, which reciprocates in direction (2) and (42) corresponding to the x-axis, and to rotary solenoid 230, which can turn about its axis as shown in FIGS. 21A and B. Cutting bed vise 63 is synchronized with reciprocating blade assembly 250 and the indexing mechanism such that the vise closes to hold suture 6 in place during cutting and opens to allow suture 6 to be advanced by the indexer to the next cutting position.

Linear solenoid 220 and rotary solenoid 230 may be adjusted to control the linear stroke and blade angle of arm 225 of reciprocating blade assembly 250 to allow for varying the depth of the barbs cut in the y and z axes. In addition, rotation of rotary solenoid 230 allows barbs to be cut in the opposite direction along the axis of suture 6 as shown in FIG. 21B. The blade angle and stroke may also be adjusted to sever suture 6 at any desired length.

FIG. 22 shows a rotational indexing mechanism for advancing suture 6. In FIG. 22, suture 6 is shown advancing around a rotating drum 210, while reciprocating blade assembly 250 cuts barbs along the axis of suture 6. Suture 6 is fed onto drum 210 and into cutting channel 215 via suture supply spool 300. Barbed suture is wound off drum 210 onto take-up spool 310. Spools 300 and 310 may supply and take up suture 6 in an untwisted state, or alternatively, either or both spools may be rotated in such a way as to twist and untwist suture 6 to allow spiral cut barbs as described above.

While the invention has been described in connection with what is considered to be the most practical and preferred embodiment, it should be understood that this invention is not to be limited to the disclosed embodiment, but on the contrary, is intended to cover various modifications and equivalent arrangements included within the spirit and scope of the appended claims.

The invention claimed is:

1. A method of cutting barbs on a suture having a longitudinal axis, said method comprising the steps of:
   providing a suture having a lateral x-axis, a forward y-axis, and a downward z-axis;
   providing a cutting blade;
   creating a barb on said suture by the motion of the blade which takes into account a cutting action by the blade on the suture in three dimensions along the x-y-z axes of the suture caused by blade geometry in conjunction with blade motion, with the blade having motion at least along the x-axis; and
   providing a means for moving the blade to cause said cutting action to create the barb;
   wherein the blade motion and blade geometry each cause the cutting in at least one of the x-, y-, and z-axes.

2. The method as described in claim 1 wherein the blade geometry causes the cutting action along the y and z axes with the blade motion causing the cutting action along the x-axis.

3. The method as described in claim 2 which includes the further step of providing a plurality of blades each of which creates a respective barb on the suture.

4. The method as described in claim 1 wherein the blade geometry causes a cutting action on the suture along one axis with the motion of the blade causing a cutting action along the remaining two axes.

5. The method as described in claim 1 wherein the y-axis is the longitudinal axis of the suture, the x-axis is perpendicular to the longitudinal axis and the z-axis is at 90° with respect to the x-axis.

6. The method as described in claim 5 wherein the blade geometry causes the cutting action along the z-axis with the blade motion causing the cutting action along the x and y axes.

7. The method as described in claim 6 which includes the further step of providing a plurality of blades each of which creates a respective barb on the suture.

8. The method as described in claim 1, further comprising a step of providing a securing means for securing the suture for cutting.

9. The method as described in claim 1 which includes the further step of rotating said suture about its longitudinal axis before or after cutting.

10. The method as described in claim 1 which includes the further step of articulating said cutting blade.

11. The method as described in claim 1 which includes the further step of advancing said suture along its longitudinal axis before or after cutting.

12. The method as described in claim 1 which includes the further step of cutting a plurality of barbs, wherein the barbs are of varying sizes.

13. The method as described in claim 1 which includes the further step of twisting said suture along its longitudinal axis prior to cutting.

14. The method as described in claim 13 which includes the further step of untwisting said suture after cutting.

15. The method as described in claim 1 wherein said cutting blade is selected from the group consisting of an articulating blade, a reciprocating blade, a rotating blade, and a hollow ground blade.

16. The method as described in claim 15, wherein when the blade is a hollow ground blade, the blade has a concave face.

17. The method as described in claim 1 which includes the further step of providing a cutting template for directing the motion of the blade.

18. The method as described in claim 1 which includes the further step of providing a solenoid as a means for moving the blade.

19. The method as described in claim 18, wherein the solenoid comprises a linear solenoid.

20. The method as described in claim 18, wherein the solenoid comprises a rotary solenoid.

21. A method of cutting barbs on a suture having a longitudinal axis, said method comprising the steps of:
   providing a suture having a lateral x-axis, a forward y-axis, and a downward z-axis;
   providing a cutting blade, wherein said cutting blade is selected from the group consisting of an articulating blade, a reciprocating blade, a rotating blade, and a hollow ground blade;
   twisting said suture along the y-axis prior to cutting;
   creating a barb on said suture by the motion of the blade which takes into account a cutting action by the blade on the suture in three dimensions along the x-y-z axes of the suture caused by blade geometry in conjunction with blade motion; and providing a means for moving the blade to cause said cutting action to create the barb.

22. The method as described in claim 21, wherein when the blade is a hollow ground blade, the blade has a concave face.

23. A method of cutting barbs on a suture having a longitudinal axis, said method comprising the steps of:
   providing a suture having a lateral x-axis, a forward y-axis, and a downward z-axis;
   providing a cutting blade;
   twisting said suture along the y-axis prior to cutting;
   providing a cutting template for directing the motion of the blade;
   creating a barb on said suture by the motion of the blade which takes into account a cutting action by the blade on the suture in three dimensions along the x-y-z axes of the suture caused by blade geometry in conjunction with blade motion; and
   providing a means for moving the blade to cause said cutting action to create the barb.

24. A method of cutting barbs on a suture having a longitudinal axis, said method comprising the steps of:
   providing a suture having a lateral x-axis, a forward y-axis, and a downward z-axis;
   providing a cutting blade;
   twisting said suture along the y-axis prior to cutting;
   creating a barb on said suture by the motion of the blade which takes into account a cutting action by the blade on the suture in three dimensions along the x-y-z axes of the suture caused by blade geometry in conjunction with blade motion; and
   providing a solenoid operatively connected to the blade for moving the blade to cause said cutting action to create the barb.

25. The method as described in claim 24, wherein the solenoid comprises a linear solenoid.

26. The method as described in claim 24, wherein the solenoid comprises a rotary solenoid.

27. A method of cutting a barb on a suture, said method comprising the steps of:
   providing a suture having a longitudinal axis;
   twisting said suture along its longitudinal axis;
   providing a cutting blade, wherein said cutting blade is selected from the group consisting of an articulating blade, a reciprocating blade, a rotating blade, and a hollow ground blade; and
   cutting a barb with said blade on said suture when in its twisted state.

28. The method as described in claim 27, wherein when the blade is a hollow ground blade, the blade has a concave face.

29. A method of cutting a barb on a suture, said method comprising the steps of:
   providing a suture having a longitudinal axis;
   twisting said suture along its longitudinal axis;
   providing a cutting blade;
   providing a cutting template for directing the motion of the blade; and
   cutting a barb with said blade on said suture when in its twisted state.

30. A method of cutting a barb on a suture, said method comprising the steps of:
   providing a suture having a longitudinal axis;
   twisting said suture along its longitudinal axis;
   providing a cutting blade;
   providing a solenoid operatively connected to the blade for moving the blade; and
   cutting a barb with said blade on said suture when in its twisted state.

31. The method as described in claim 30, wherein the solenoid comprises a linear solenoid.

32. The method as described in claim 30, wherein the solenoid comprises a rotary solenoid.

33. A twist-cut spiral barbed suture made by a process comprising the steps of:
   providing a suture having x-y-z axes;
   providing a cutting blade;
   twisting said suture along the y-axis prior to cutting;
   creating a barb on said suture by the motion of the blade which takes into account a cutting action by the blade on the suture in three dimensions along the x-y-z axes of the suture caused by blade geometry in conjunction with blade motion; and
   providing a means for moving the blade to cause said cutting action to create the barb.

34. The twist-cut spiral barbed suture made by the process as described in claim 33 wherein the blade geometry causes a cutting action on the suture along two axes with the motion of the blade causing a cutting action along the remaining axis.

35. The twist-cut spiral barbed suture made by the process as described in claim 33 wherein the y-axis is the longitudinal axis of the suture, the x-axis is perpendicular to the longitudinal axis and the z-axis is at 90° with respect to the x-axis.

36. The twist-cut spiral barbed suture made by the process as described in claim 35 wherein the blade geometry causes the cutting action along the y and z axes with the blade motion causing the cutting action along the x-axis.

37. The twist-cut spiral barbed suture made by the process as described in claim 36, wherein the process includes the further step of providing a plurality of blades each of which creates a respective barb on the suture.

38. The twist-cut spiral barbed suture made by the process as described in claim 33 wherein the blade geometry causes a cutting action on the suture along one axis with the motion of the blade causing a cutting action along the remaining two axes.

39. The twist-cut spiral barbed suture made by the process as described in claim 33 wherein the y-axis is the longitudinal axis of the suture, the x-axis is perpendicular to the longitudinal axis and the z-axis is at 90° with respect to the x-axis.

40. The twist-cut spiral barbed suture made by the process as described in claim 39 wherein the blade geometry causes the cutting action along the z-axis with the blade motion causing the cutting action along the x and y axes.

41. The twist-cut spiral barbed suture made by the process as described in claim 40 wherein the process includes the further step of providing a plurality of blades each of which creates a respective barb on the suture.

42. The twist-cut spiral barbed suture made by the process as described in claim 33, wherein the process further comprises a step of providing a securing means for securing the suture for cutting.

43. The twist-cut spiral barbed suture made by the process as described in claim 42, wherein said securing means provides for relative rotation as between the suture and the cutting blade.

44. The twist-cut spiral barbed suture made by the process as described in claim 33 wherein the process includes the further step of rotating said suture about its longitudinal axis before or after cutting.

45. The twist-cut spiral barbed suture made by the process as described in claim 33 wherein the process includes the further step of articulating said cutting blade.

46. The twist-cut spiral barbed suture made by the process as described in claim 33 wherein the process includes the further step of advancing said suture along its longitudinal axis before or after cutting.

47. A twist-cut spiral barbed suture made by a process comprising the steps of:
 providing a suture having a longitudinal axis;
 twisting said suture along its longitudinal axis; and
 cutting a barb on said suture when in its twisted state.

48. The twist-cut spiral barbed suture made by the process in accordance with claim 47 wherein the process includes the further step of cutting a plurality of barbs on said suture when in its twisted state.

49. The twist-cut spiral barbed suture made by the process in accordance with claim 47 wherein the process includes the further step of advancing said suture along its longitudinal axis before or after cutting.

50. A twist-cut spiral barbed suture having a longitudinal axis and made by a process comprising the steps of:
 providing a suture:
 providing a cutting blade;
 twisting said suture along its longitudinal axis prior to cutting;
 creating a barb on said suture by the motion of the blade which takes into account a cutting action by the blade on the suture in three dimensions along x-y-z axes of the suture; and
 providing a means for moving the blade to cause said cutting action to create the barb,
 wherein the motion of the blade causes cutting along the x-y-z axes.

51. The twist-cut spiral barbed suture made by the process as described in claim 50 wherein the process includes the further step of providing a plurality of blades each of which creates a respective barb on the suture.

52. The twist-cut spiral barbed suture made by the process as described in claim 50 wherein the process includes the further step of untwisting said suture after cutting.

* * * * *